United States Patent [19]
Menon

[11] Patent Number: 6,059,832
[45] Date of Patent: May 9, 2000

[54] PROSTHETIC WRIST IMPLANTS, INSTRUMENTS, AND RELATED METHODS OF IMPLANTATION

[75] Inventor: Jay Menon, Claremont, Calif.

[73] Assignee: Kinetikos Medical, Incorporated, San Diego, Calif.

[21] Appl. No.: 08/806,265

[22] Filed: Feb. 24, 1997

Related U.S. Application Data

[63] Continuation-in-part of application No. 08/605,525, Feb. 23, 1996, Pat. No. 5,702,470.

[51] Int. Cl.⁷ ........................................................ A61F 2/42
[52] U.S. Cl. ................................................................ 623/21
[58] Field of Search ................................ 623/18, 19, 20, 623/21, 22, 23, 66; 128/898

[56] References Cited

U.S. PATENT DOCUMENTS

| | | |
|---|---|---|
| 3,875,594 | 4/1975 | Swanson . |
| 4,106,128 | 8/1978 | Greenwald et al. . |
| 4,158,893 | 6/1979 | Swanson . |
| 4,164,793 | 8/1979 | Swanson . |
| 4,178,640 | 12/1979 | Buechler et al. . |
| 4,198,713 | 4/1980 | Swanson . |
| 4,784,661 | 11/1988 | Beckenbaugh et al. . |
| 5,314,485 | 5/1994 | Judet . |
| 5,326,364 | 7/1994 | Clift, Jr. et al. . |
| 5,507,821 | 4/1996 | Sennwald et al. . |

FOREIGN PATENT DOCUMENTS

| | | |
|---|---|---|
| 0034192 | 8/1981 | European Pat. Off. . |
| 92/00709 | 1/1992 | WIPO . |

Primary Examiner—David J. Isabella
Assistant Examiner—Choon P. Koh
Attorney, Agent, or Firm—Baker & Maxham

[57] ABSTRACT

Prosthetic wrist implants, instruments, and methods for implanting the wrist implant. A prosthetic wrist implant is disposed between a patient's radius and carpal complex bones. It includes a radial implant component having an elongated concave articulate front surface and a rear surface which is screwed into the radial bone. A carpal bone implant includes a base member with a front surface and a flat rear surface which is screwed into the carpal bone complex. Alternatively, a post may extend from either the back of the radial implant rear surface of the carpal bone implant, or both, and be implanted into the radial bone or the carpal bone respectively. An articulating bearing member having a flat bottom surface is fastened to the front surface of the carpal bone implant base member and an elongated convex surface slidingly engages the concave articular surface of the radial implant to permit articulation between the radial and carpal bones.

22 Claims, 25 Drawing Sheets

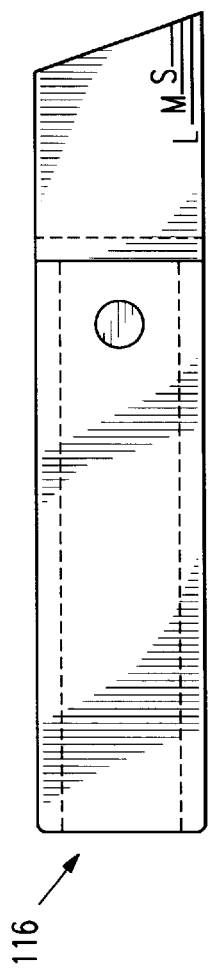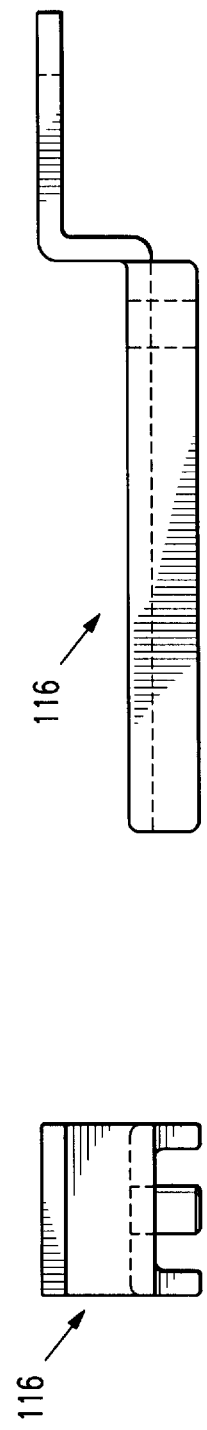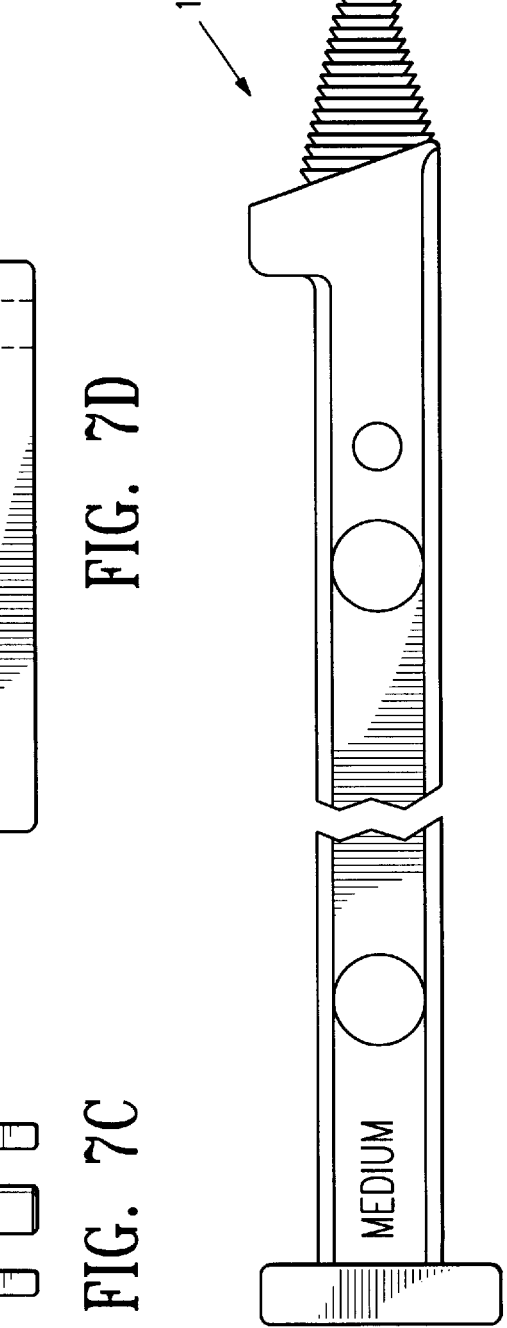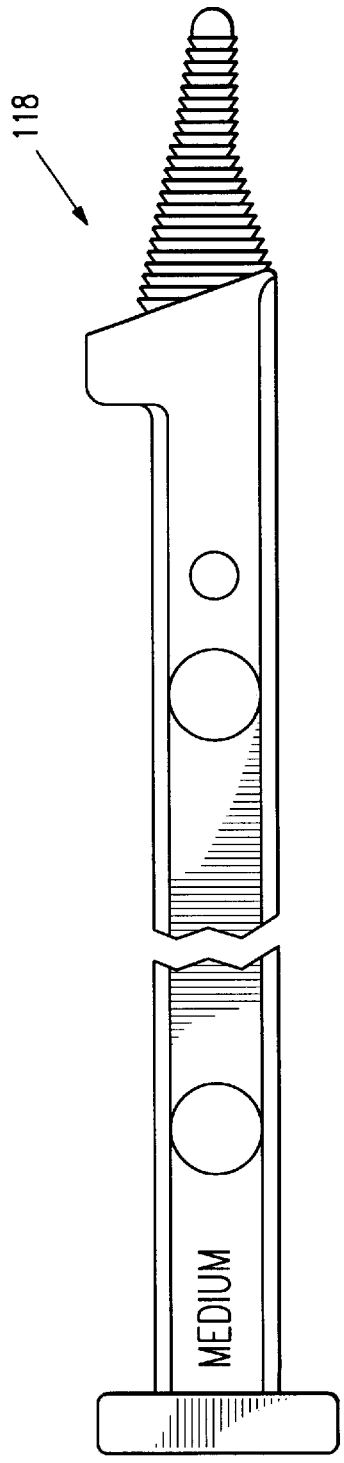
FIG. 7A
FIG. 7B
FIG. 7C
FIG. 7D
FIG. 7E

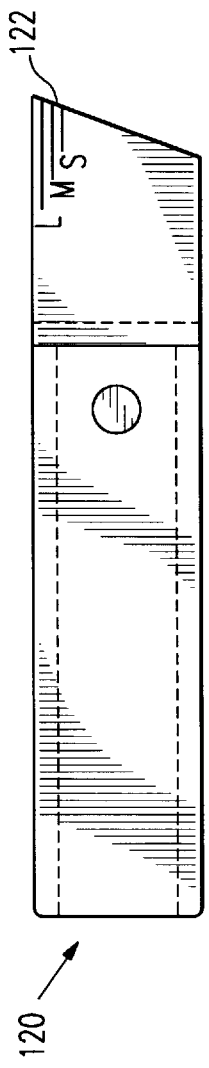
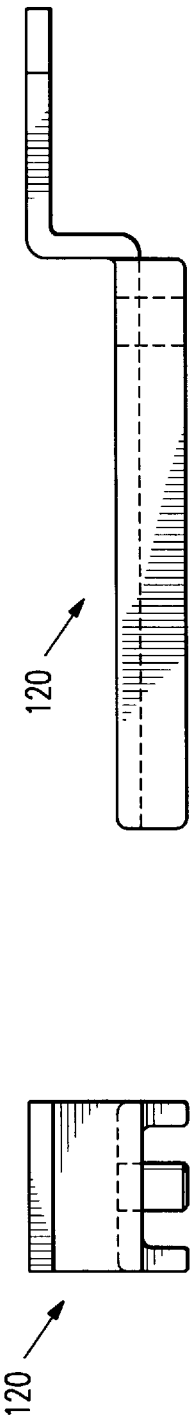
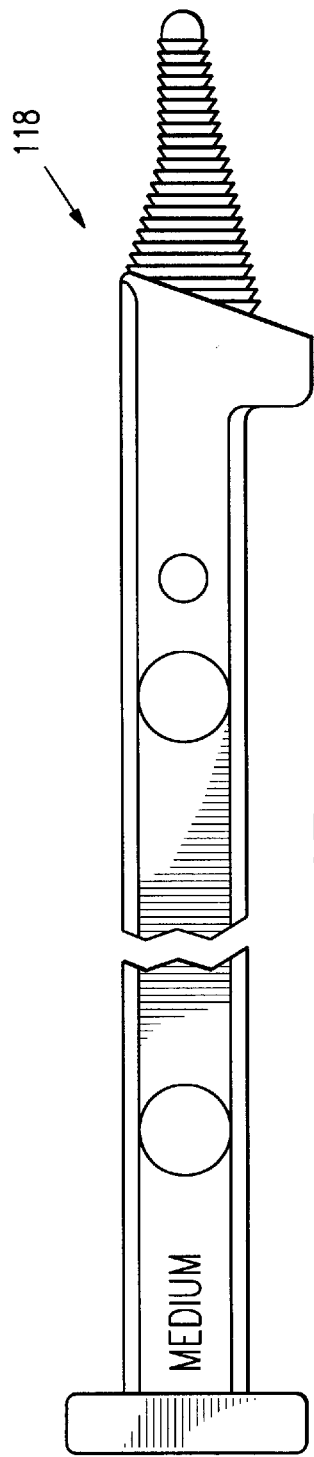
FIG. 8A
FIG. 8B
FIG. 8C
FIG. 8D
FIG. 8E

LARGE

MEDIUM

SMALL

WRONG

DORSAL

CORRECT

WRONG

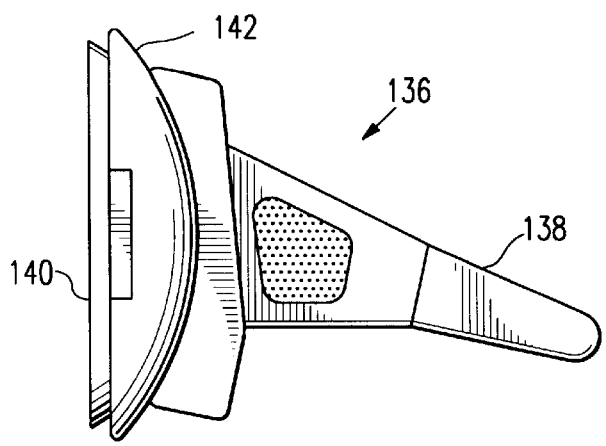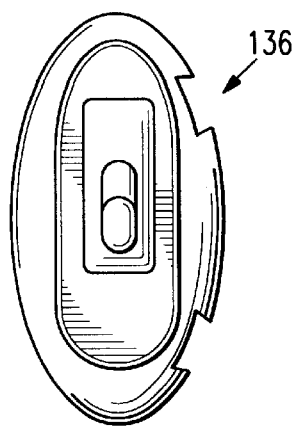
FIG. 25   FIG. 26
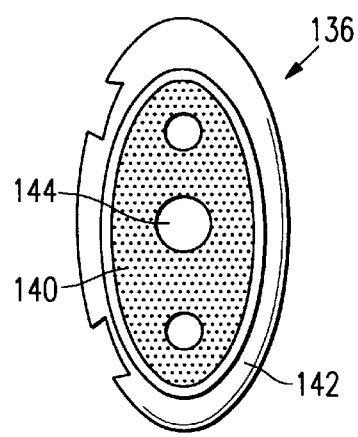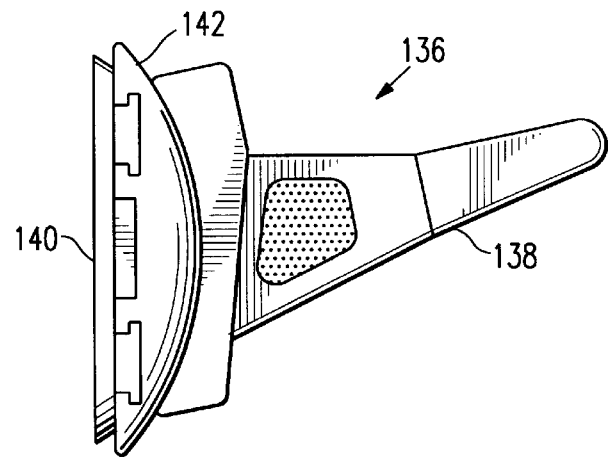
FIG. 27   FIG. 28
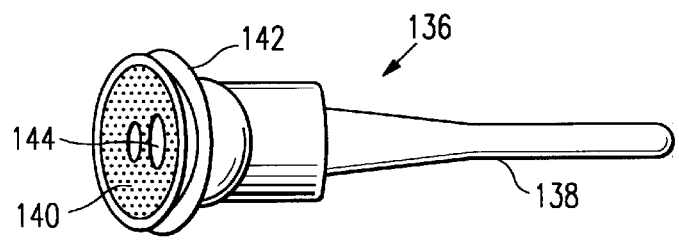
FIG. 29
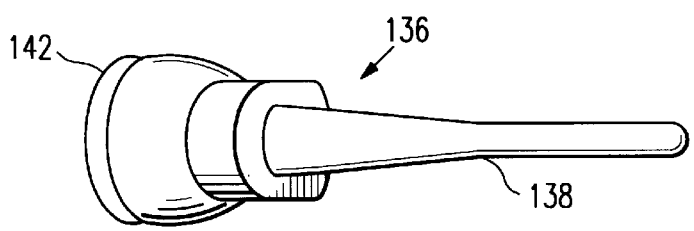
FIG. 30

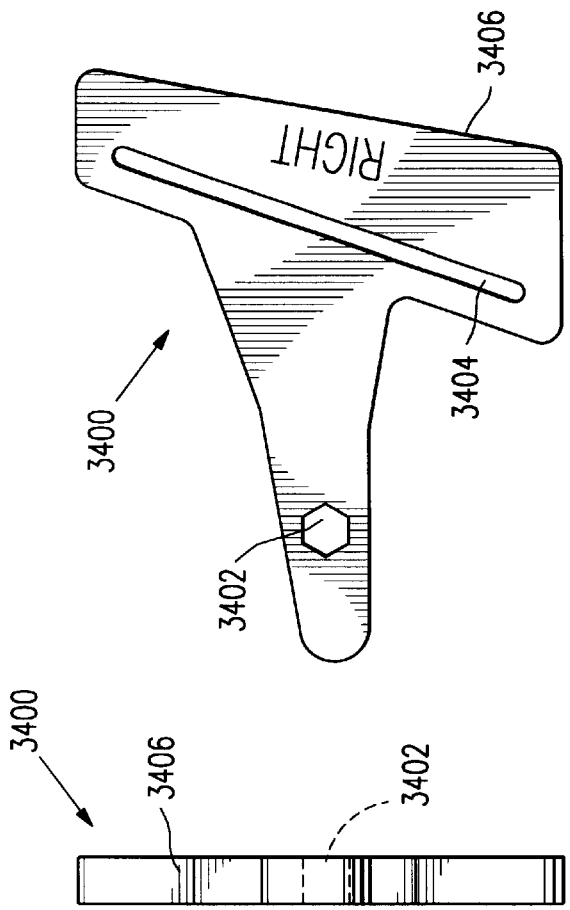
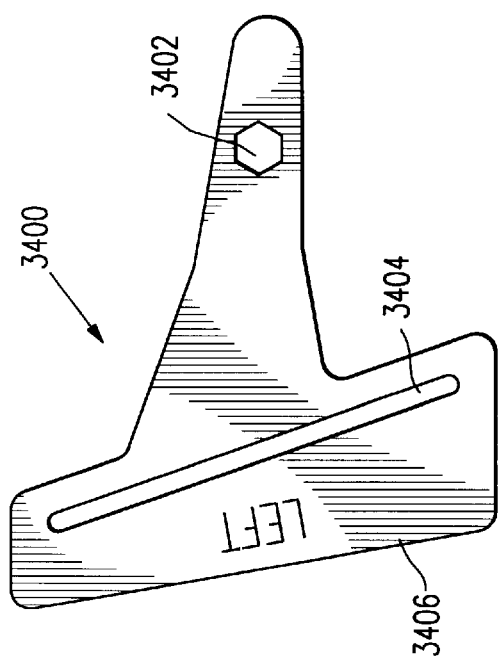
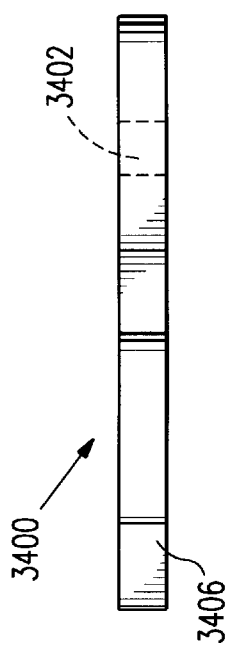
FIG. 32C
FIG. 32B
FIG. 32A
FIG. 32D

PROSTHETIC WRIST IMPLANTS, INSTRUMENTS, AND RELATED METHODS OF IMPLANTATION

CROSS-REFERENCES TO RELATED APPLICATIONS

This application is a continuation-in-part of an application, Ser. No. 08/605,525, filed with the United States Patent and Trademark Office on Feb. 23, 1996, U.S. Pat. No. 5,702,470.

BACKGROUND OF THE INVENTION

1. Field of the Invention

This invention relates to prosthetic implants and more particularly to a prosthetic wrist implant with a geometry that closely matches that of the natural wrist and which minimizes bone resection. The invention also includes methods and instruments used to perform the implantation of the prosthesis.

2. Description of the Related Art

The replacement of degenerated natural joints with man made prosthetic replacements is well known, including the replacement of the wrist joint. Prior to the introduction of prosthetic joint replacement, patients with wrists diseases such as radio-carpal arthritis were often treated with a fusion procedure. Fusion involves an implantable joint replacement that prevents articulation of the wrist. Fusion however, was less than satisfactory since it left the patient with no movement in the wrist.

Existing prosthetic wrist implants have a number of drawbacks. Because of the size needed to achieve the necessary strength, wrist implants have typically required excessive amounts of bone to be resected. For example, in these implants relatively large and lengthy implant stems were inserted into the radius and carpal bones. This significantly weakened the bones making them more susceptible to post operative fracture. Furthermore, once fracture occurs, because of the significant loss of bone due to resection, their may not be enough bone left to permit a satisfactory fusion procedure. This may leave a patient without any avenue of treatment, not even fusion.

Another drawback with prior prosthetic wrist implants is that they do not provide the patient with acceptable functionality. Part of the problem is that these implants have not adequately matched the geometry of the natural wrist. As a result, flexion and extension of the hand, return to a natural position, and range of motion have all been less than optimum, and the patient is left with less functionality of the implanted wrists than with a natural wrist.

Another difficulty with prior wrist implants involves the means of attaching the implant to the radius and carpal bones. If the attachment is not secure enough, or the implant itself is not strong enough, the stability of the attachment may not be adequate under normal use of the wrist. Because of this, larger implants and implant stems have been used to attach the implant components into the bone. However, as discussed above, this results in more resection and weakening of the bone. As a result of the above issues, existing prosthetic wrist implants have not always achieved adequate levels of patient satisfaction and have sometimes resulted in unacceptable complication rates.

Another problem with wrist implant procedures is the unavailability of special instruments for performing the implant operations. Tools currently available make excavation of a hole, which is cut into the bone to position the implant, difficult and imprecise. As a result, malrotation of the tool may occur which results in misalignment of the implant. Further, specialty templates are unavailable to assist in alignment of a cutting blade during resection of the bone into which the implant is to be fitted. The absence of a template during the actual resection requires the surgeon performing the resection to "eyeball" the area to be resected. This may result in excess bone material being removed during the resection.

Thus, it would be desirable to provide an improved prosthetic wrist implant, method, and instruments which overcome some or all of the above-discussed problems. In particular it would be desirable to provide a wrist implant which has a geometry which matches that of a natural wrist and which affords the patient a natural range of motion, natural flexion and natural extension of the hand. Furthermore, it would be desirable to provide a prosthetic wrist implant which is small enough to minimize the bone resection required. It would also be desirable to provide an improved method for attaching a prosthetic wrist implant which provides a stable and strong attachment to the bone without requiring excessive loss of bone through resection or drilling. In addition it would be desirable to provide instruments for implanting a prosthetic wrist implant which minimizes bone loss from resection and which affords the patient the above-described desirable features.

SUMMARY OF THE INVENTION

The prosthetic wrist implant of the present invention combines a number of positive design features to provide an implant having an optimal range of motion with acceptable flexion and extension of the hand. It does this by incorporating a unique geometry that matches that of the natural wrist. For example, an inclined articular surface of the radial component of the implant mimics the articular surface of the radius. In addition, the prosthetic wrist implant of the present invention incorporates an improved technique for attaching to the bone which utilizes a combination of posts and screws. Alternatively, screws alone can be used to attach the implant to the bone. This, coupled with the small size of the implant, minimizes the bone resection and bone loss. This results in a stronger attachment as well as stronger bone structure post operatively.

The instruments of the present invention also offer a number of positive design features to assist in performing the implant surgery. In one embodiment, rasps of varying sizes are used for reaming the medullary canal of the radius bone. For example, a starter rasp is used to centrally position the hole within the medullary canal. Thereafter, rasps of increased size are used to slowly enlarge the hole until the hole is slightly larger than the implant post to be inserted. Furthermore, in preparing the radial bone for excavation of the medullary canal, a template may be positioned on the radial bone to guide the cutting tool during resection.

In accordance with one embodiment of the present invention, the prosthetic wrist implant comprises a radial implant having an elongated concave articular front surface and a back surface having a first flat face and a second flat face tilted at an angle with respect to the first flat face. The radial implant also has a first post member projecting from the second flat face into a cavity in the radial bone. The wrist also includes a carpal bone implant including a planar member having a front face and a generally flat rear face, and a second post member projecting from the rear face into a cavity into the carpal bone complex. In an alternative embodiment, neither the radial bone implant nor the carpal bone implant use post members to assist in securing the implant to the respective bones. Instead, screws are used. The wrist implant also includes an articulating member having a flat bottom surface fastened to the front face of the planar member and an elongated convex surface slidingly engaging the concave articulating surface of the radial implant to permit articulation between the radial and carpal bone complex along the articular surfaces. In a preferred embodiment the carpal bone implant planar member has two openings therein and a pair of screws inserted through the two planar member openings into the carpal bone complex.

The details of the preferred embodiment of the present invention are set forth in the accompanying drawings and the description below. Once the details of the invention are known, numerous additional innovations and changes will become obvious to one skilled in the art.

BRIEF DESCRIPTION OF THE DRAWING

FIGS. 7A–7E are various views of a radius cutting guide and broach used for the left radius in accordance with the method of the present invention.

FIGS. 8A–8E are various views of a radius cutting guide and broach used for the right radius in accordance with the method of the present invention.

FIG. 25 is a top view of the prosthetic wrist implant of FIG. 24.

FIG. 26 is a rear view of the prosthetic wrist implant in accordance with the embodiment of FIG. 24.

FIG. 27 is a front view of the prosthetic wrist implant shown in FIG. 24.

FIG. 28 is a bottom view of the prosthetic wrist implant of FIG. 24.

FIG. 29 is a right side elevational view of the prosthetic wrist implant of FIG. 24.

FIG. 30 is a left side elevational view of the prosthetic wrist implant of FIG. 24.

FIGS. 32A–32D are side views of a template in accordance with one embodiment of the present invention.

Like referenced numbers and designations in the various drawings refer to like elements.

DETAILED DESCRIPTION OF THE PREFERRED EMBODIMENTS

The present invention is for a prosthetic wrist implant, a method for performing the operation of implanting the prosthetic wrist implant and instruments to assist in performing the operation. The prosthetic wrist implant and the instruments of the present invention minimize bone resection and allow natural articulation of the hand. It has a geometry which matches that of a natural wrist to afford a natural range of motion to the patient. An inclined articular surface of the radial component of the implant mimics the articulate surface of the radius. It's small size and method of attachment minimizes bone resection. It may utilize screws for attachment of the carpal component, the radial component, or both, and provides a stable and strong attachment with minimal drilling.

Figure 1:
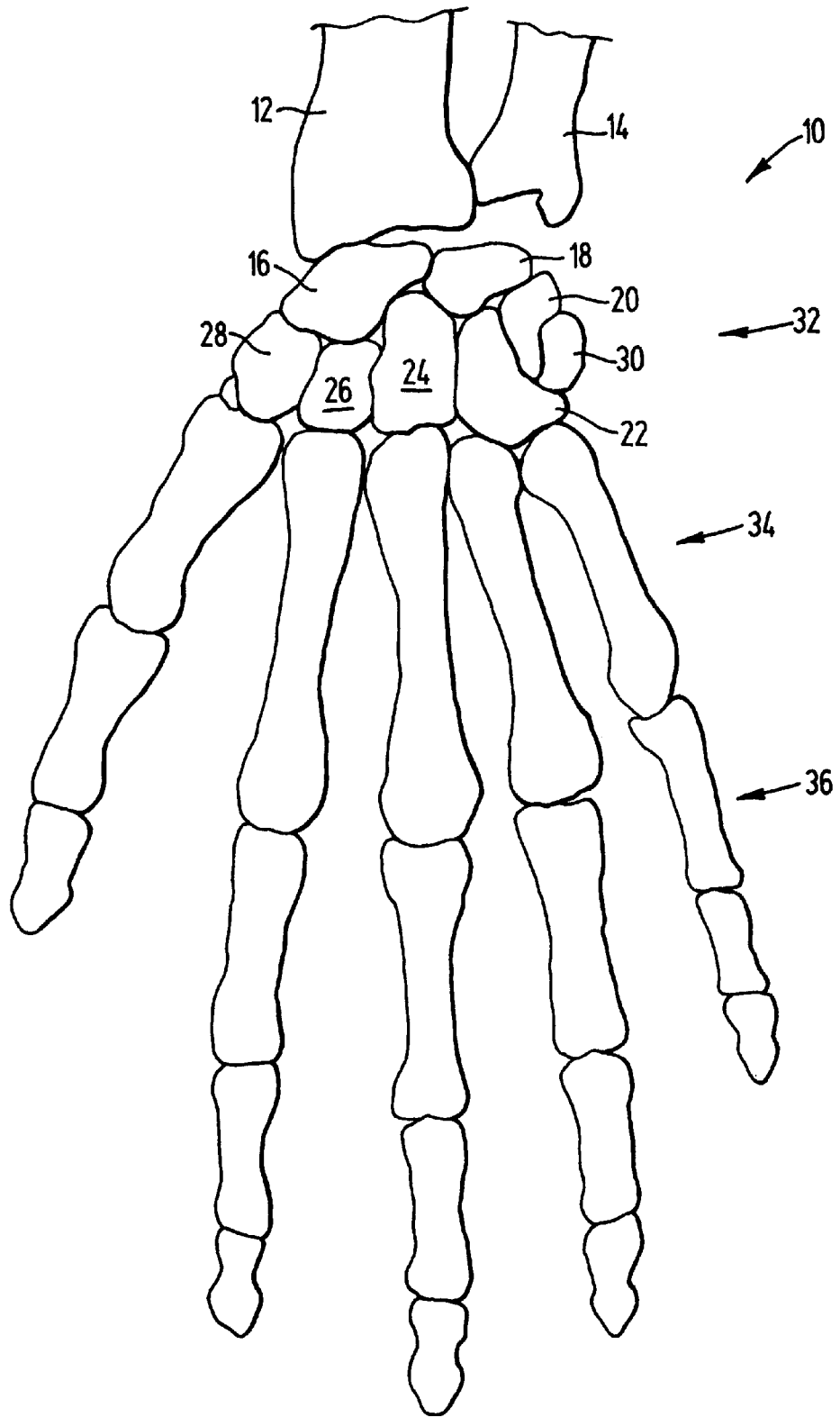
FIG. 1 is a drawing of the bones of the left hand dorsal surface.

Referring now to FIG. 1 there is shown the bones of the left hand viewing the dorsal surface and including the radius and ulnar. In particular, FIG. 1 shows the bones of the wrist 10 which includes the radius 12, the ulna 14, the scaphoid 16, the lunate 18, the triquetrum 20, the hamate 22, the capatate 24, and the lesser 26 and greater 28 trapezoid bones. Also shown is pisiform bone 30. These eight bones 16–30 make up the carpus 32 of the hand. Additional bones which will not be discussed in detail include the metacarpus bones 34 and the phalanges bones 36.

It will be appreciated that the scaphoid 16 and lunate 18 bones articulate with the radius 12 to provide motion of the wrists. In a variety of wrists disorders, such as radio-carpal arthritis, patients may experience discomfort, pain and difficulty in moving the wrist. Prior surgical treatment of this condition involves fusion which, as discussed previously, will prevent articulation of the scaphoid and lunate bones with the radius. In this procedure, the patient may have their pain alleviated, but is left without motion of the wrists. This severely restricts the patient's use of their wrist.

Subsequently, prosthetic wrist implants have been developed to provide an artificial articulating surface for the wrists. However, previous implants have suffered from a number of drawbacks such as those discussed above including limited range of motion and excessive bone resection which significantly weakens the bones in question and subjects them to a greater likelihood of fracture.

Thus, in accordance with the present invention an improved prosthetic wrist implant is provided which minimizes the amount of bone which is resected and which provides the patient with a very natural range of motion and flexion. It does this by its unique geometry, small size and unique method of attachment.

Figure 2A:
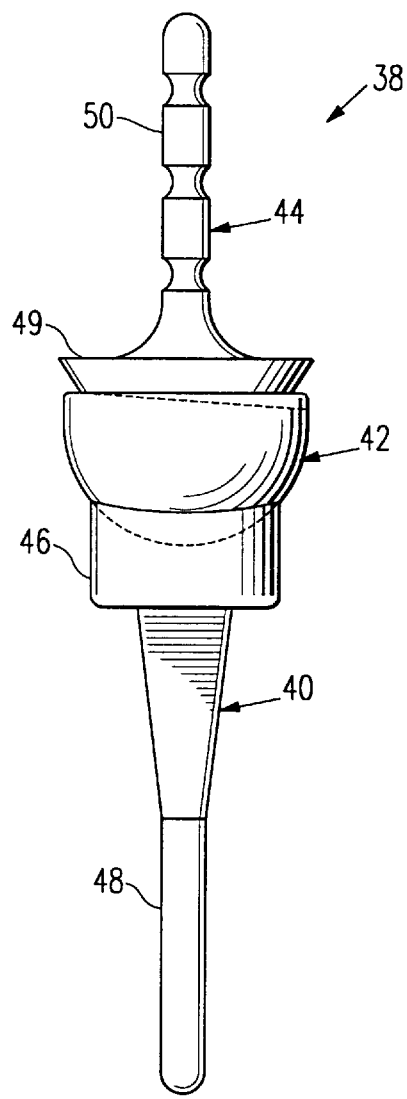
FIGS. 2A–2B are side and front elevational views of the components of the prosthetic wrist implant in accordance with a preferred embodiment of the present invention.
Figure 2B:
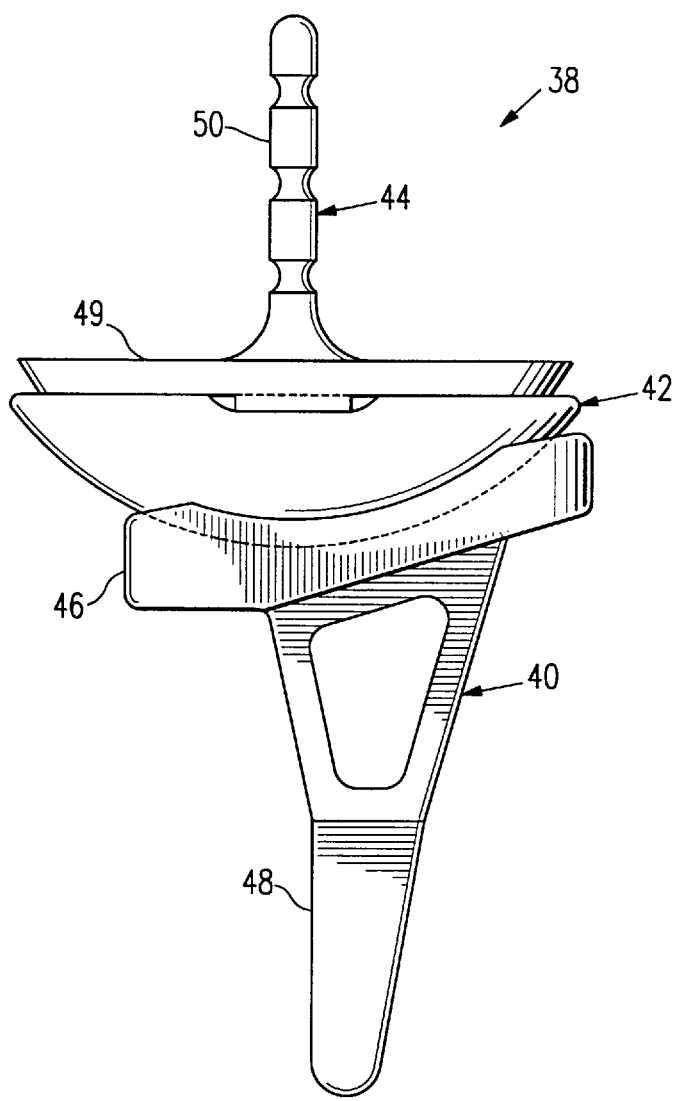

Referring now to FIGS. 2A and 2B one embodiment of the prosthetic wrist implant of the present invention 38 is shown. In FIG. 2A, a side view of the wrist implant 38 shows the three components including a radial implant 40, a bearing component 42 and a carpal implant 44. Similarly, FIG. 2B shows these three components in a front view. It is notable that, as best as seen in the front view, the prosthetic wrist implant 38, incorporates a bearing guide 46 which is tilted with respect to the axis of the radius into which a radius post 48 is inserted. The carpal implant component 44 includes a flat base member 49 and a post member 50 which is inserted into the carpus 32. The bearing 42 is mounted affixedly to the flat carpal base member 49 and provides a self-lubricating surface which is articulated against the bearing guide 46.

Figure 3A:
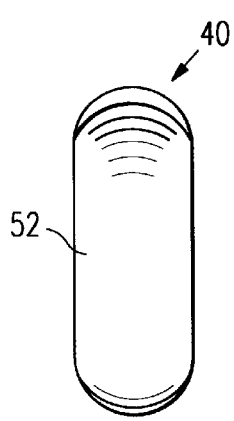
FIGS. 3A–3E are various views of the radial implant component of the present invention.
Figure 3B:
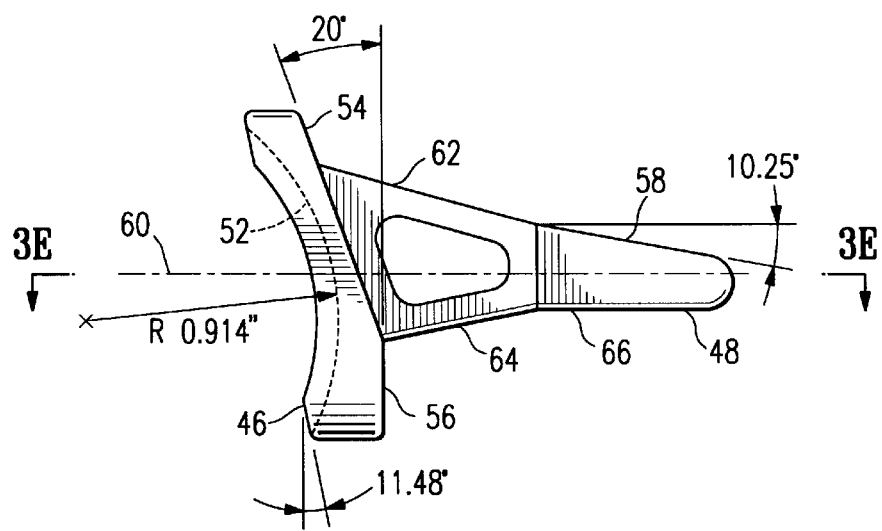
Figure 3D:
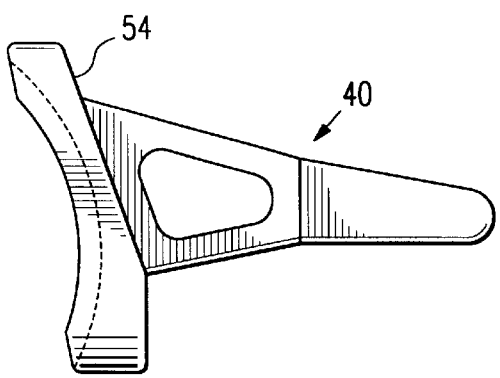
Figure 3C:
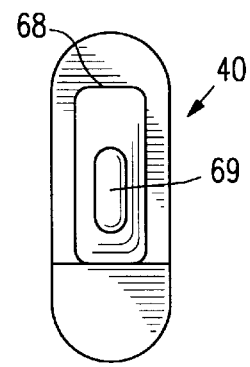
Figure 3E:
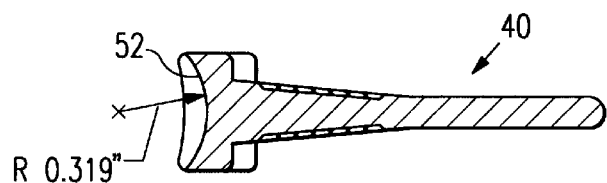

Referring now to FIGS. 3A–3E, one embodiment of the radial implant component 40 is shown in more detail. FIG. 3A shows the bearing guide 46 which preferably includes a concaved bearing surface 52. As shown in FIG. 3B, this curved surface 52, in the preferred embodiment, has a radius of 0.914 inches. The bearing guide 46 is preferably disposed at approximately a 11.5 degree angle also has a back face 54 which abuts against the surface of the radius bone 12 as described in more detail below. A second flat surface 56 of the bearing guide 46 is disposed at a 20 degree angle with the bearing guide back surface 54. The radial post 48 is attached to the bearing guide back surface 54 and includes a post surface 58 which is preferably at approximately a 10.25 degree angle with respect to the axis of the radius 60. The post 48 also is preferably generally tapered from the back bearing guide surface 54 at surfaces 62, 64 and 66 as shown in FIG. 3B. As shown in FIG. 3C, the radial post 48 preferably tapers down from its attachment from the shape shown at 68, where it is attached to the face 54, down to a rounded end portion 69. FIG. 3D is similar to FIG. 3B with additional dimensions and angles of the preferred embodiment shown. FIG. 3E is a side sectional view of the radial implant 40 showing that the bearing articulating surface 52 along the side axis has a radius of approximately 0.319 inches. In the preferred embodiment radial implant, 40 is made of titanium such as Ti-6AI-4V(F136). However, it will be appreciated by those skilled in the art that other materials having sufficient strength and biocompatability may also be employed.

Figure 4A:
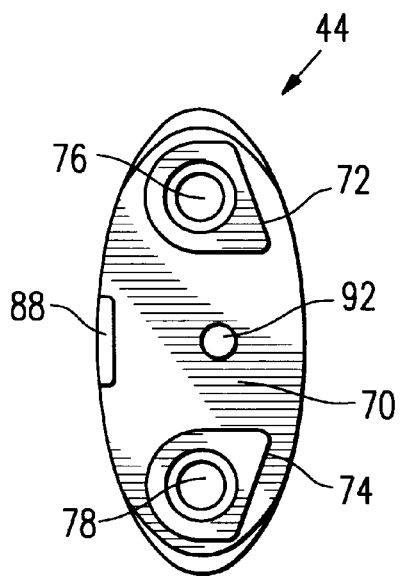
FIGS. 4A–4D are various views of the carpal implant component of the present invention.
Figure 4B:
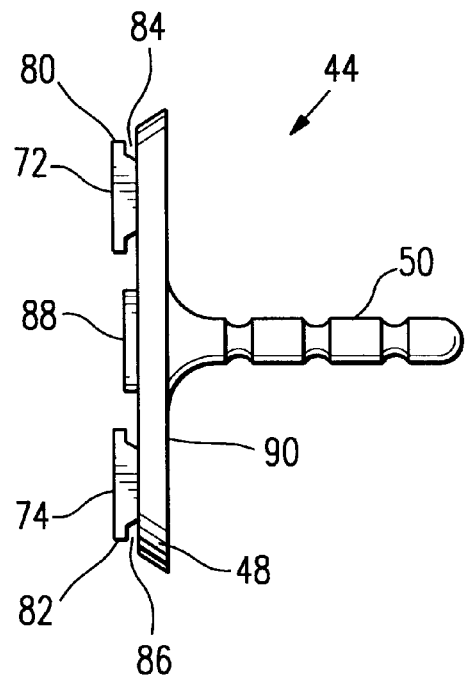

Referring now to FIGS. 4A–4D, the carpal implant component 44 of the present invention is shown. As shown in FIG. 4A, the carpal implant 44 includes a front face 70 which is preferably attached to the carpal bearing 42 by means of locking tabs 72 and 74. Locking tabs 72 and 74 also preferably have tapered holes 76 and 78 through which attachment screws (described below) are inserted into the carpal bones. As shown in more detail in FIG. 4B, locking tabs 72 and 74 preferably include a raised head portion 80 and 82 and slots 84 and 86. In the preferred embodiment, the raised head portions 80 and 82 and slots 84 and 86 are configured to engage with slots in the carpal bearing 42 as described in more detail below. Tab 88 is a slightly raised tab which also engages with a slot in the carpal bearing as described below. Carpal post 50 protrudes perpendicularly from the back face 90 of the carpal implant 44. Also shown in FIG. 4A opening 92 which is threaded and may be used to attach an instrument to facilitate pushing the carpal implant 44 into the carpal bone.

Figure 4C:
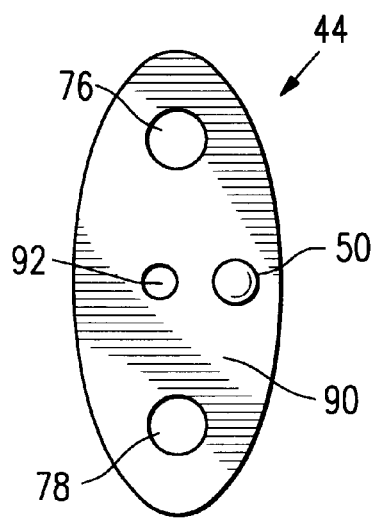
Figure 4D:
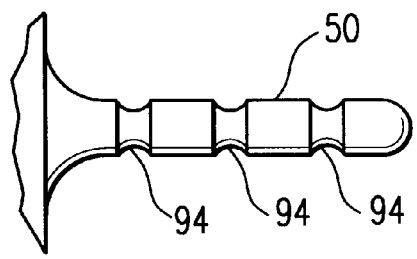

FIG. 4C shows the location of the opening 92 and the post 50 of the preferred embodiment when viewed from the back surface 90 of the carpal implant. Referring now to FIG. 4D, the carpal post 50 is shown including a series of grooves 94 which serve to secure the post 50 into the carpal bone once it is implanted such as with cement. In particular, post 50 is preferably inserted into the capitate bone 24 as described in more detail below. Likewise, the screws inserted into holes 76 and 78 are screwed into the hamate 22 and trapezoid bones as described in more detail below. The carpal implant 42 is likewise preferably made of the same material as the radial implant 40, such as titanium.

Figure 5A:
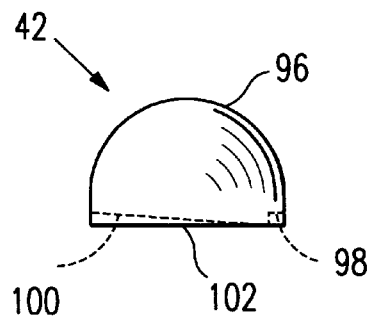
FIGS. 5A–5C are various views of the carpal bearing component of the present invention.
Figure 5B:
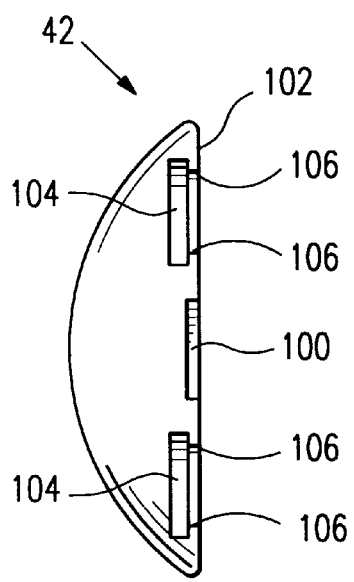
Figure 5C:
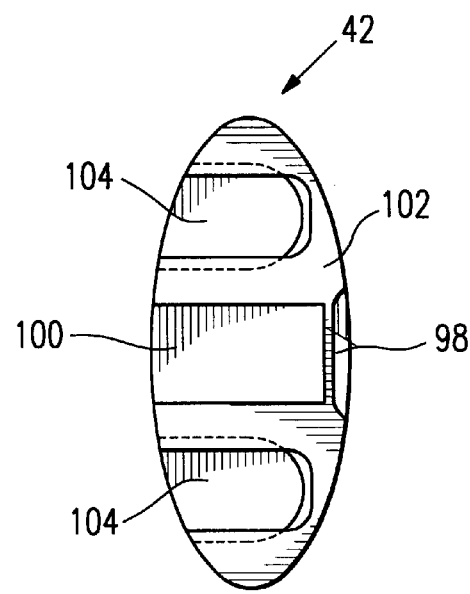

Referring now to FIGS. 5A–5C, the preferred embodiment of the carpal bearing 42 is shown. The carpal bearing 42 as seen in FIG. 5A in end view has a convex articulating surface 96 which has a radius of approximately 0.314 inches. Also a small slot 98 is preferably on one edge of the carpal bearing 42, and a tapered recess 100 is located on the carpal bearing bottom face 102. As shown in FIGS. 5B and 5C, the carpal bearing bottom surface 102 also preferably includes slots 104, having a lip portion 106. When installing the carpal bearing 42 on to the carpal implant 44, the slots 104 engage with the raised tabs 72, 74 as the carpal bearing is slid sideways over the carpal implant front surface 70. Likewise, tab 88 will engage with tapered slot 100 creating increasingly strong pressure as the tab 88 slides up the ramp of tapered slot 100. When fully engaged across the surface 70, the carpal tab 88 will drop down and lock into slot 98 thereby preventing the carpal bearing 42 from being removed. Also, it should be noted that the lip portion 106 will engage below the raised portions 80, 82 thereby preventing the carpal bearing 42 from separating from the face 70 once installed. Carpal bearing 42 in the preferred embodiment is made ultra high molecular weight polyethylene (UHMWPe). However, it will be appreciated that other self-lubricating plastic materials may also be employed. In addition, other materials such as metal may also be used in some situations. The carpal bearing 42 imitates the articulation of the lunate and scaphoid bones.

Figure 6:
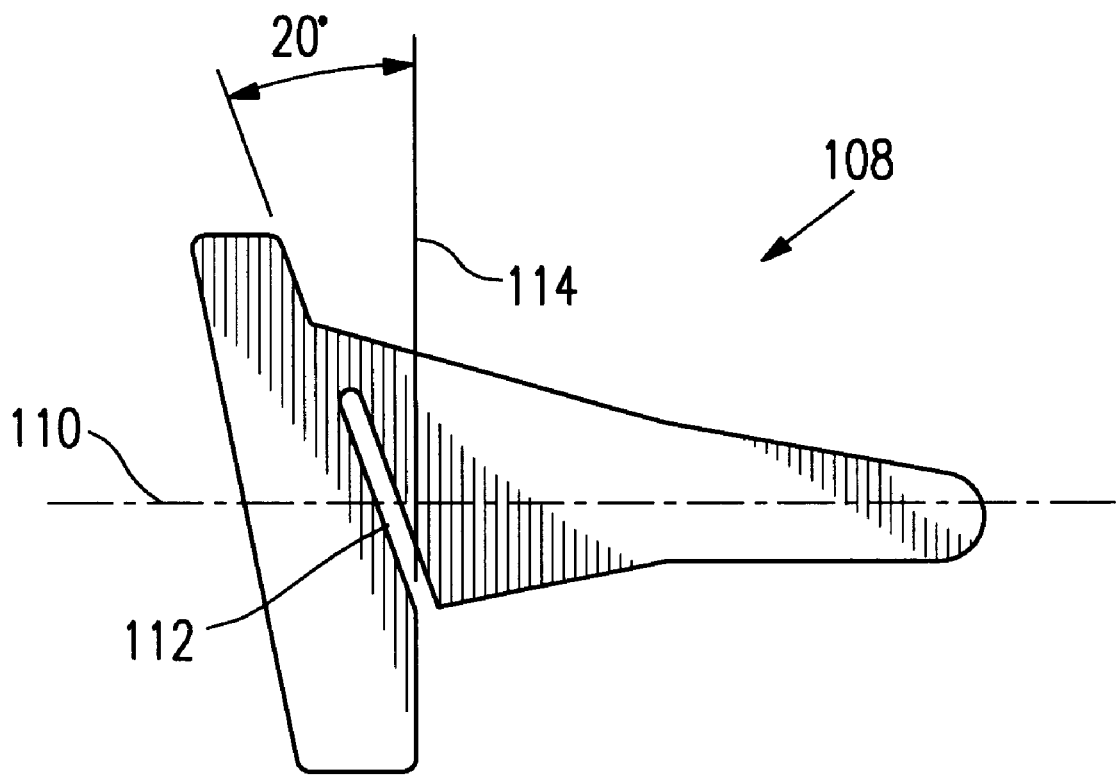
FIG. 6 is a side elevational view of a radial body templet for performing radial resection in accordance with a preferred method of the present invention.

Referring now to FIG. 6, there is shown a radial body templet which is used to determine the correct angle at which to resect the radial bone. Where the axis of the radius is shown at line 110, the resection cut of the radius will be made along slot 112. This cut will be at a 20 degree angle with the line 114, which is normal to the radius bone axis 110. Radial body templet 108 is preferably made of ⅛ stainless steel.

Referring now to FIGS. 7A–7E, there is shown various views of a radius cutting guide for use on a left radius bone in a manner described below. Shown in FIG. 7E is a broach 118 used for resecting the radius bone interior as described in more detail below. FIGS. 8A–8D show a radius cutting guide 120 which is the same as radius cutting guide 116 except that it is used on the right radius. Note that marks 122 on the radius cutting guide indicate three positions depending on the size of the patient and corresponding size of implants, designated small, medium and large (SML). This guide would thereby control the depth of the cutting of broach 118 shown in FIG. 8E.

Figure 9C:
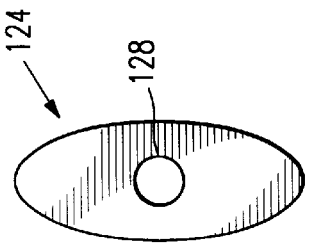
FIGS. 9A–9C are various views of a radial pusher bearing used for installing the radial component of the present invention.
Figure 9B:
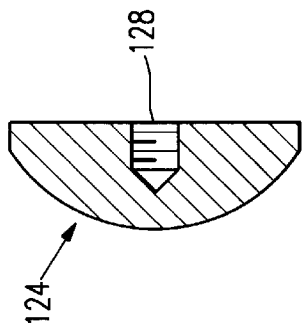
Figure 9A:
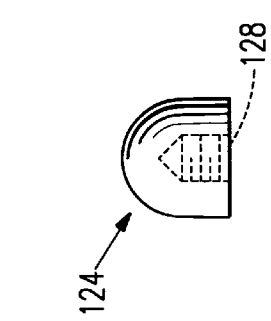
Figure 10:
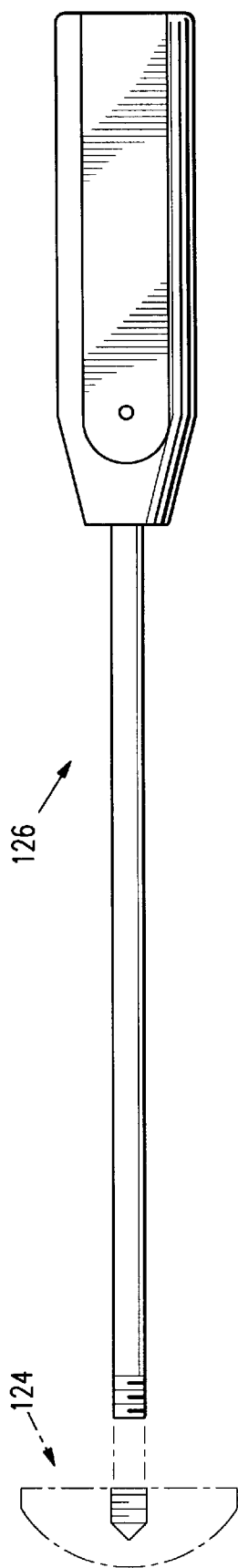
FIG. 10 is a side elevational view of a radial pusher handle used with the radial pusher bearing in FIGS. 9A–9C.
Figure 11A:
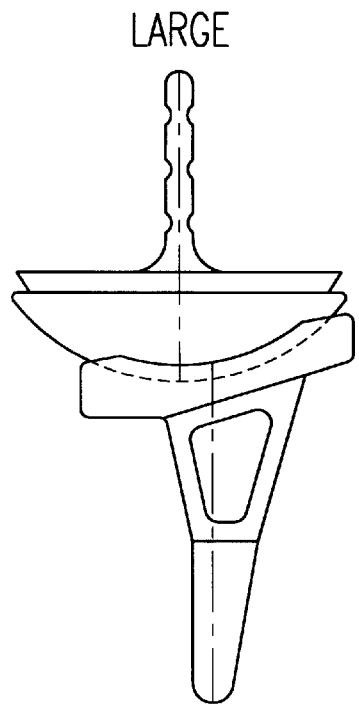
FIGS. 11A–11F show x-ray templets used for three sizes of the present invention.
Figure 11B:
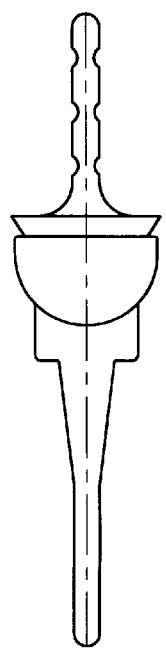
Figure 11C:
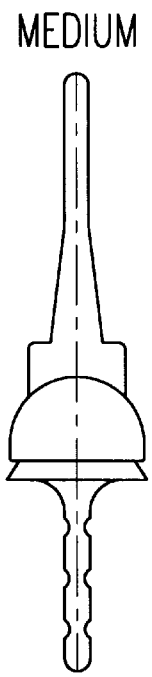
Figure 11D:
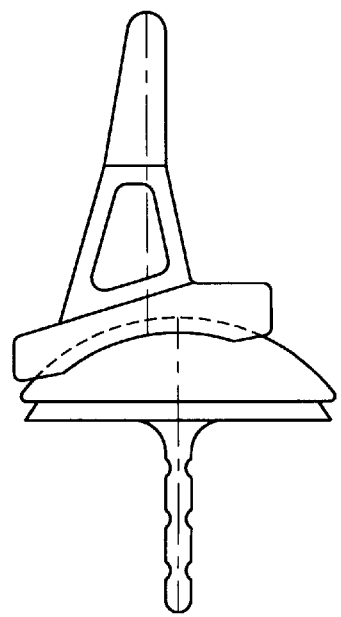
Figure 11E:
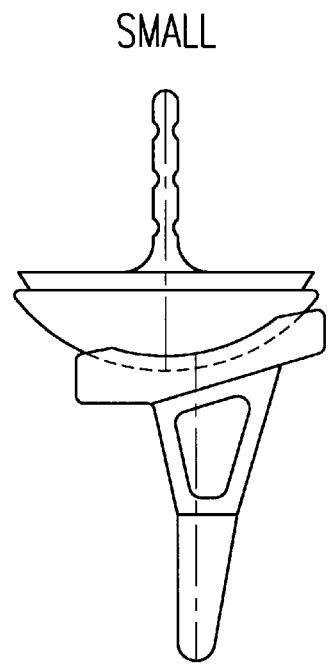
Figure 11F:
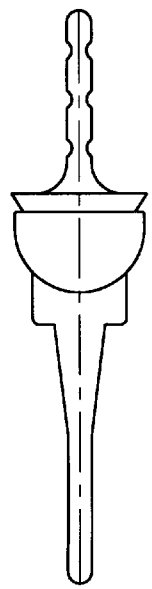

FIGS. 9A–9C show various views of a radial pusher bearing 124 which will be used in so conjunction with radial pusher handle 126, shown in FIG. 10. In particular, radial pusher handle 126 is threaded into opening 128 in the radial pusher bearing 126 and is used to push the carpal implant post 50 into the capitate bone.

FIGS. 11A–11F illustrate x-ray templets used in conjunction with the prosthetic wrist implant 38 to ensure proper sizing of the implant prior to the surgical operation of as discussed in more detail below. Small, medium and large sizes of the implants are shown in two views in the x-ray templet.

The surgical technique of implanting the prosthetic wrist implant 38 of the present invention will now be described in connection with FIGS. 12–21. Prior to performing the prosthetic wrist implant surgical procedure in accordance with the present invention, the patient is placed under general anesthesia. Alternatively auxiliary block anesthesia may be used. A tourniquet is used to obtain a bloodless field. Prior to the procedure, x-ray templets as shown in FIGS. 11A–11F are used to determine the correct size (for example small, medium and large) of the wrist prosthesis.

Figure 12:
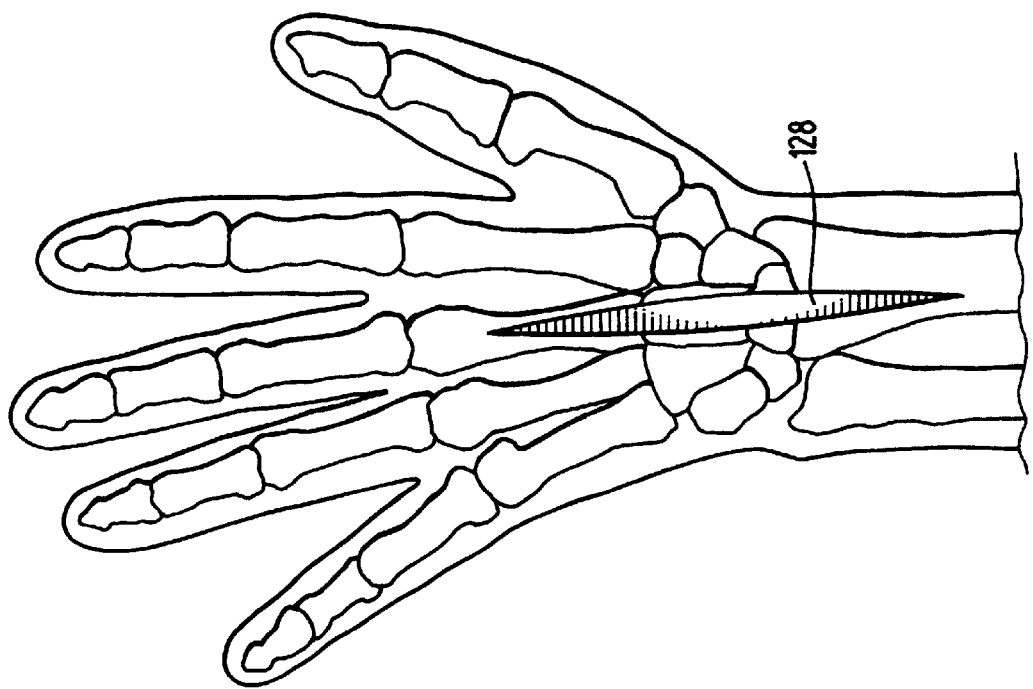
FIG. 12 is a phantom view of the left hand showing the surgical incision utilized in accordance with the method of the present invention.
Figure 15:
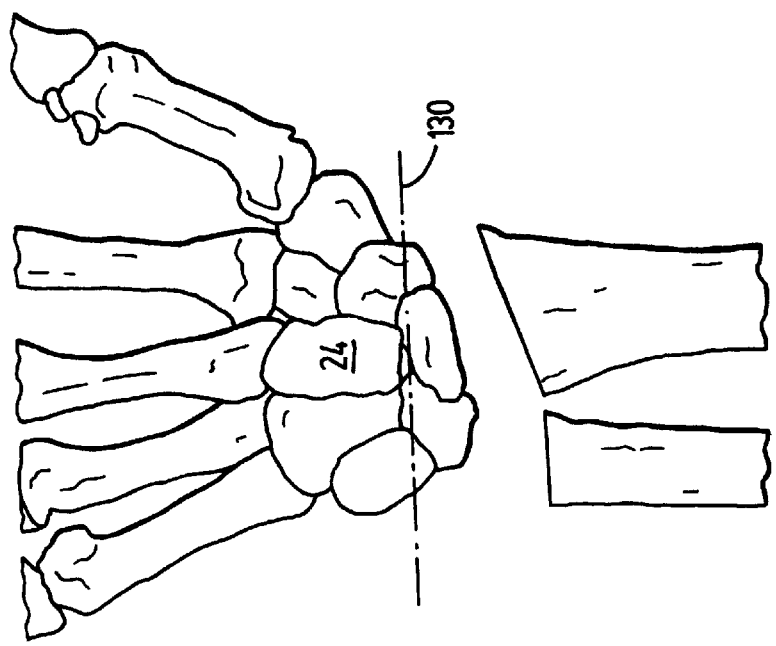
FIG. 15 is a perspective view of the bones of the left hand illustrating the carpal resection in accordance with the method of the present invention.

Referring now to FIG. 12 a longitudinal dorsal incision 128 is made over the wrist along the line of the third metacarpal. Subcutaneous tissue and skin are elevated sharply from the extensor tendons and retracted medially and laterally using three zero silk retraction sutures. The extensor retinaculum is opened up in a step cut fashion so that one half can be utilized to close the joint capsule. The extensor retinaculum is opened over the fourth compartment and raised medially and laterally. A dorsal synovectomy is carried out and the wrist extensors are checked for structural integrity.

Figure 13:
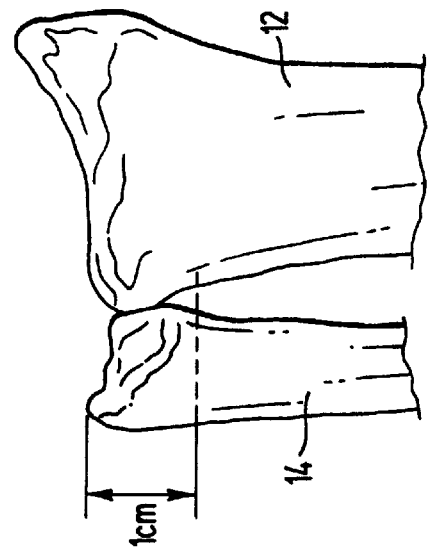
FIG. 13 is a perspective view of radius and ulnar bones showing ulnar resection in accordance with the present invention.
Figure 14:
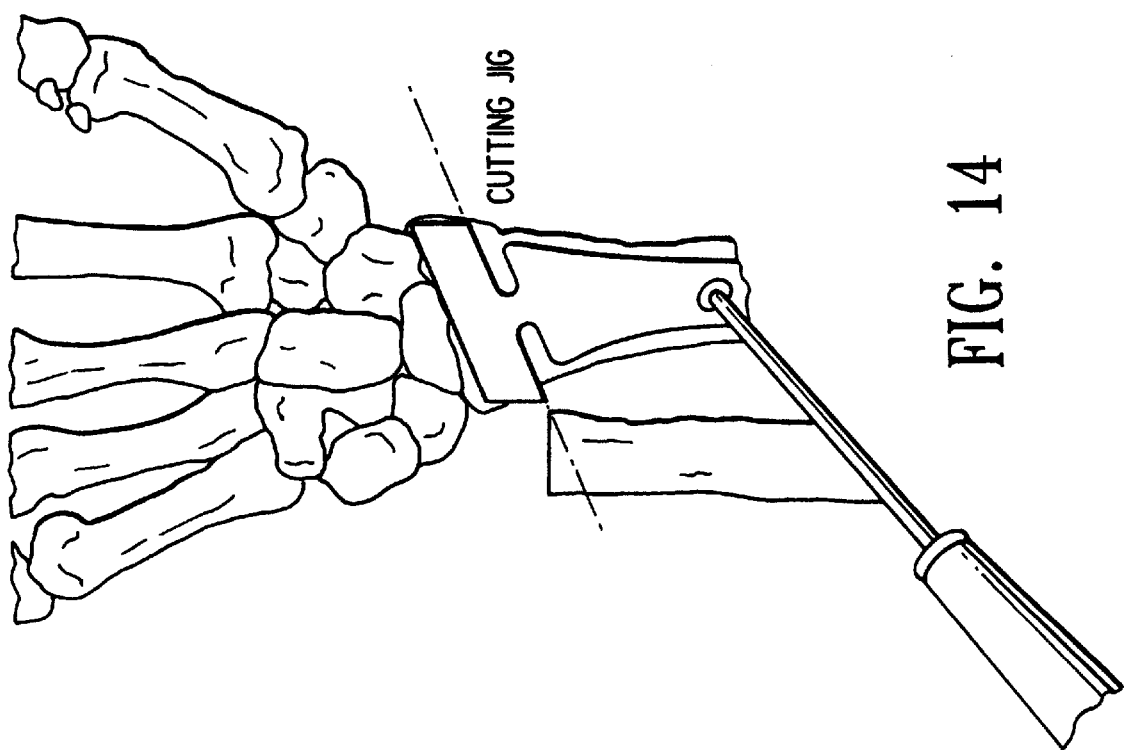
FIG. 14 is a perspective view of the bones of the left hand, the resectioned ulnar and the distal radius illustrating the resection method of the present invention.

To perform the ulnar head resection, the capsule over the distal ulna is opened longitudinally. As shown in FIG. 13, the distal one centimeter of the ulna 14 is osteotimized and removed. A synovectomy of the ulnar compartment is then performed. To perform the radial resection, the joint capsule is detached from the distal radius and left attached distally. Dissection is carried out radially. The brachioradialis is elevated and the tendons of the first dorsal compartment muscles from the styloid process are elevated subperiosteally. The branch of the posterior intraosseous nerve is resected and the accompanying vessels cauterized. A haze retractor is inserted to protect the sutures. The distal end of the radius is identified by palpation as the wrist is passively flexed and extended. Wrist joint evectomy is done. The wrist is flexed and the haze retractors on either side of the radius expose the end radial cutting jig is aligned along the longitudinal axis of the radius on the dorsal aspect of the radius as shown in FIG. 14. The dorsal lip and the radial articular surface is osteotomized and removed. The radial cutting jig weight is aligned along the longitudinal axis of the dorsal aspect of the radius. Using an oscillating saw, the line of osteotomy is marked. The jig is removed, and using the saw, the osteotomy is completed. The line of osteotomy is about 20 degrees to the longitudinal axis of the radius. Only the dorsal lip and the articular surface are removed. If necessary, additional bone is removed after the initial trial and reduction. Traction is applied to the hand by the assistant and the hand is held along the line of the forearm.

Figure 33:
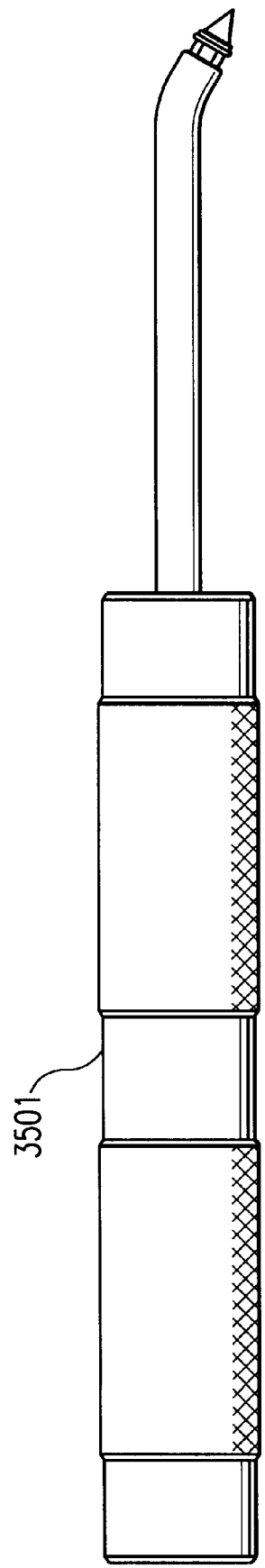
FIG. 33 is a side view of one embodiment of a template positioning tool in accordance with an alternative embodiment of the present invention.

FIGS. 32A–32D show an alternative embodiment for the radial cutting jig. The jig is aligned along the longitudinal axis of the radius on the dorsal aspect as shown in FIG. 14. Once positioned, a jig handle 3501 as shown in FIG. 33 is inserted through hole 3402 in the jig 3400. This allows the jig to be slightly rotated during resection although maintaining its overall position along the length of the radial bone. An elongated slot 3404 extends transversely across the jig's 3400 cutting plate 3406. The elogated slot 3404 allows the cutting blade of an oscillating saw to be inserted into the slot to perform an osteotomy. The jig 3400 remains in place on the radial bone during the osteotomy. After the oscillating saw is removed from the jig, the jig may be removed from the radial bone.

When performing the carpal resection, the line 130 of the osteotomy for the carpal bones passes through the proximal end of the capitate 24. The plane of the osteotomy is perpendicular to the axis of the capitate mediocarpal complex. If the carpal is subluxed, traction should be applied to the hand to bring the carpal bones from under the radius. The capitate must be positively identified prior to resection. For example, the wrist may be flexed to about 80 degrees. Part of the scaphoid and the triquetrum are left intact, along with the distal carpal bones. An intercarpal fusion is carried out by removing the cartilage from the articular surfaces of the capitate, triquetrum, hamate and the scaphoid using a burr or curette. All loose fragments of bone are removed from the joint. If there are any large defects in the volar capsule, they are then closed with absorbable sutures.

Figure 16:
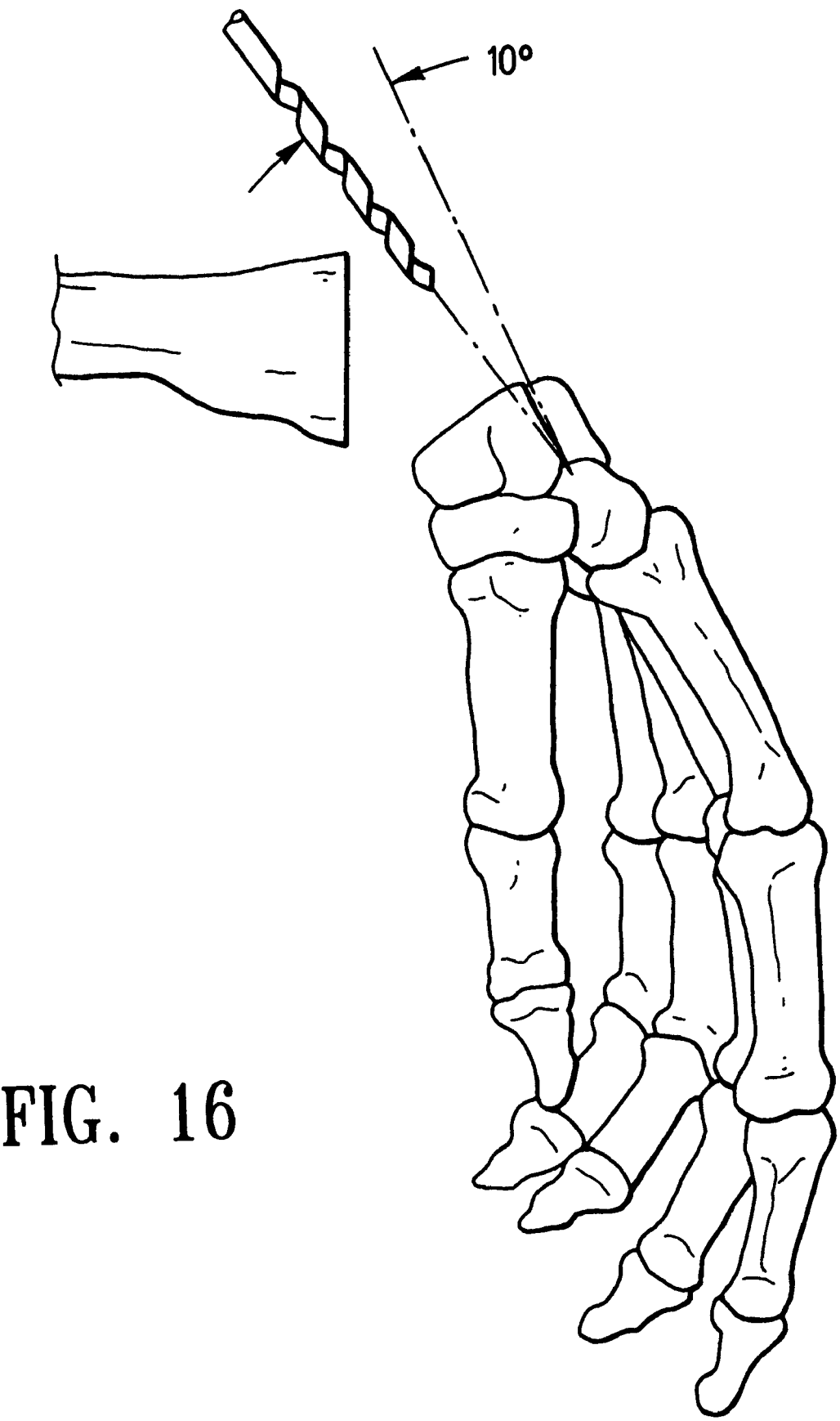
FIG. 16 is a perspective view of the bones of the left hand illustrating the technique of drilling into the center of the capitate/mediocarpal complex in accordance with the method of the present invention.

To prepare the carpal side, a hole in the center of the capitate-metacarpal complex is made using a 3.2 millimeter drill bit. In particular, the drill bit starts at the center of the capitate and proceeds into the third metacarpal. The drill needs to angled to about ten degrees dorsally to accomplish the correct alignment. As shown in FIG. 16 a probe is introduced into this hole and using an image intensifier, the position of the probe is checked. When viewed in the image intensifier, the probe must be intraosseous in both the AP and lateral planes. The hole is then enlarged to accept the stem 50 of the carpal component with a 3.5 millimeter drill bit.

Figure 17A:
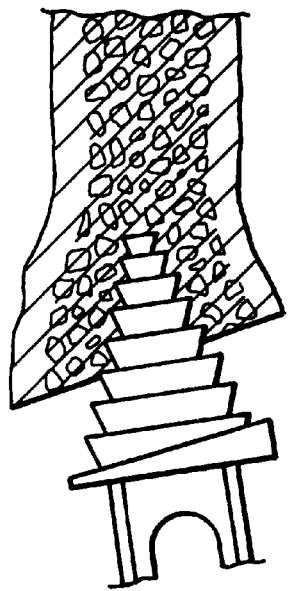
FIGS. 17A–17B illustrate the technique of preparing the radius using a broach in accordance with the method of the present invention.
Figure 17B:
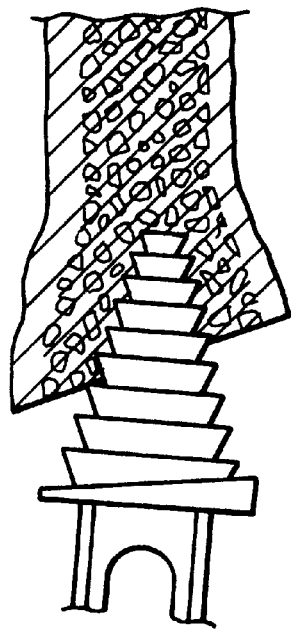
Figure 18A:
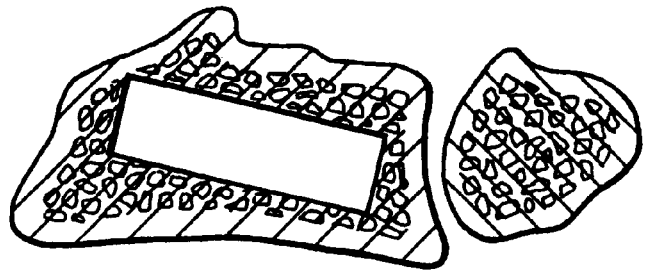
FIGS. 18A–18C illustrates correct and incorrect preparation of the radius in accordance with the method of the present invention.
Figure 18B:
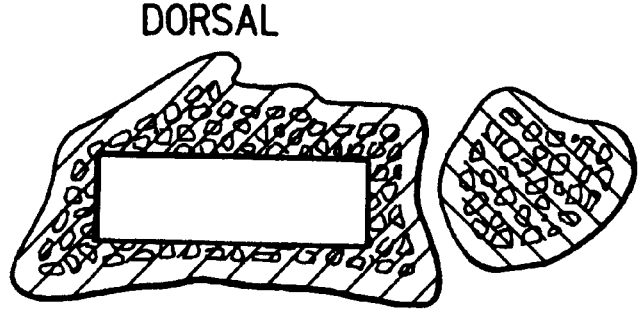
Figure 18C:
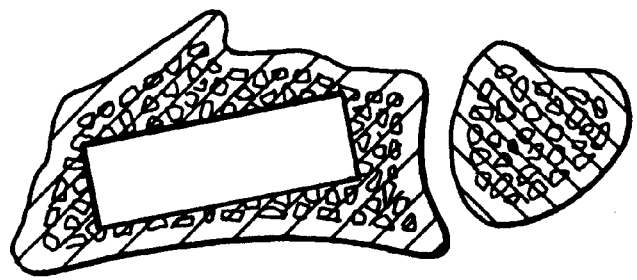

To prepare the radius as shown in FIGS. 17A and 17B, the surgeon sits at the end of the hand table in order to have a end-on view of the distal radius 12. The medullary canal of the radial bone is reamed with an appropriate size broach such as broach 118. The broach should be inserted at a valgus angle shown in FIG. 17B and not at the varus angle shown in FIG. 17A. The second radial cutting block is aligned over the broach and the radius is cut to match the contour of the radial component. FIGS. 18A–18C indicate malrotation of rasp as compared to correct positioning. That is, FIGS. 18A and 18C indicate wrong positioning and FIG. 18B indicates the correct positioning.

Figure 34:
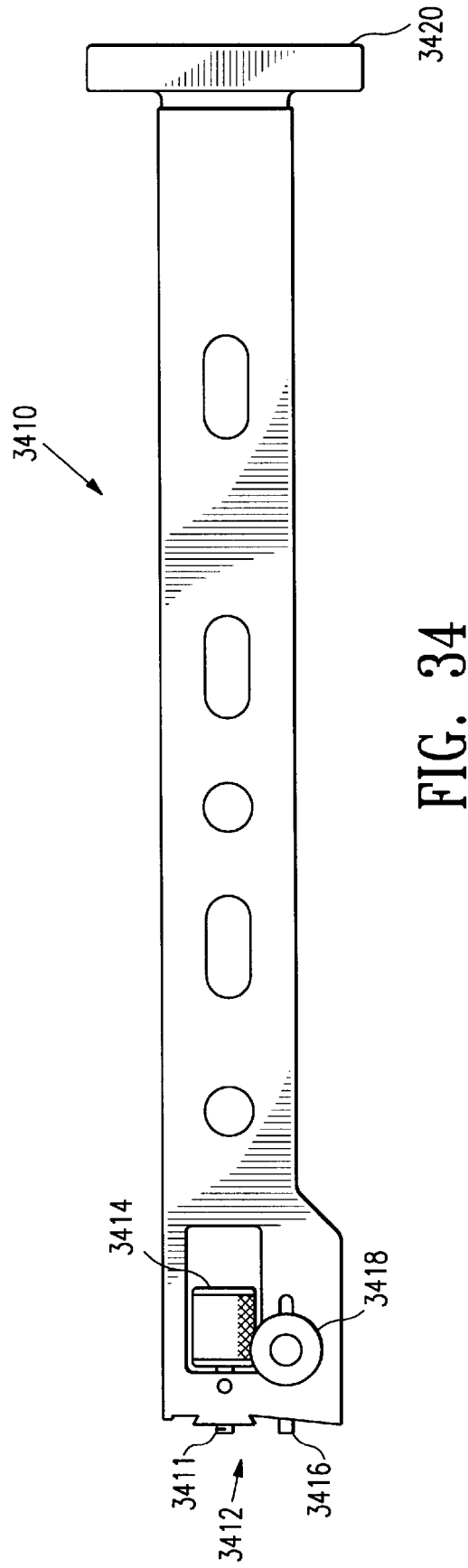
FIG. 34 is a side view of one embodiment of a rasp handle used in accordance with one embodiment of the present invention.

An alternative to using the broach 118 to ream the medullary canal of the radial bone is to use a series of differently sized rasps to perform the reaming or excavation. A rasp as shown in FIGS. 31A–31E is inserted into the medullary canal in order to position the hole to be excavated. This "starter" rasp is used to make an indentation in the medullary canal in a position which substantially correlates with the center line axis of the radial implant. The ridges 3302 shown on the rasp in FIGS. 31A–31E allow for material to be removed the medullary canal. A pointed tip 3304 of the starter rasp is pointed in order to facilitate positioning when the hole is first initiated. However, various shaped tips might be used on the rasps. On base 3306 of the rasp, opposite the pointed end of the rasp, a slot 3308 is formed into the base 3306 so that the rasp may be readily interchanged on a rasp handle shown in FIG. 34. In accordance with the preferred embodiment of the present invention, the rasp handle 3410 has a proximal end 3412 that conforms to the contour of the proximal end of each rasp. A tapped hole 3309 (see FIG. 31B) in the proximal end of the rasp mates with a threaded shaft 3411 which protrudes from the proximal end 3412 of the handle 3410. A knurled head 3414 allows the user to secure the threaded shaft 3411 into the tapped hole 3309. In addition, due to the configuration of the slot 3308 in the rasp (see FIG. 31a), the handle must slid onto each rasp. A pin 3416 which protrudes from the proximal end of the handle 3410 must be retracted in order to mate the rasp and handle 3410. The pin 3416 is retracted by moving a button 3418 fixed to the pin toward the distal end 3420 of the handle 3410.

After the initial hole has been made with the starter rasp, a rasp substantially similar in configuration to the starter rasp, with the exception that the second rasp is larger in dimensions, is inserted into the hole so that the hole in the medullary canal may be broadened. Thereafter, successively larger rasps may be used until the hole in the medullary canal has obtained an optimal size. Using multiple rasps as opposed to broach 118 allows for malrotation of the rasp to be minimized. Accordingly, correct positioning of the hole which receives the implant components is achieved.

Figure 19:
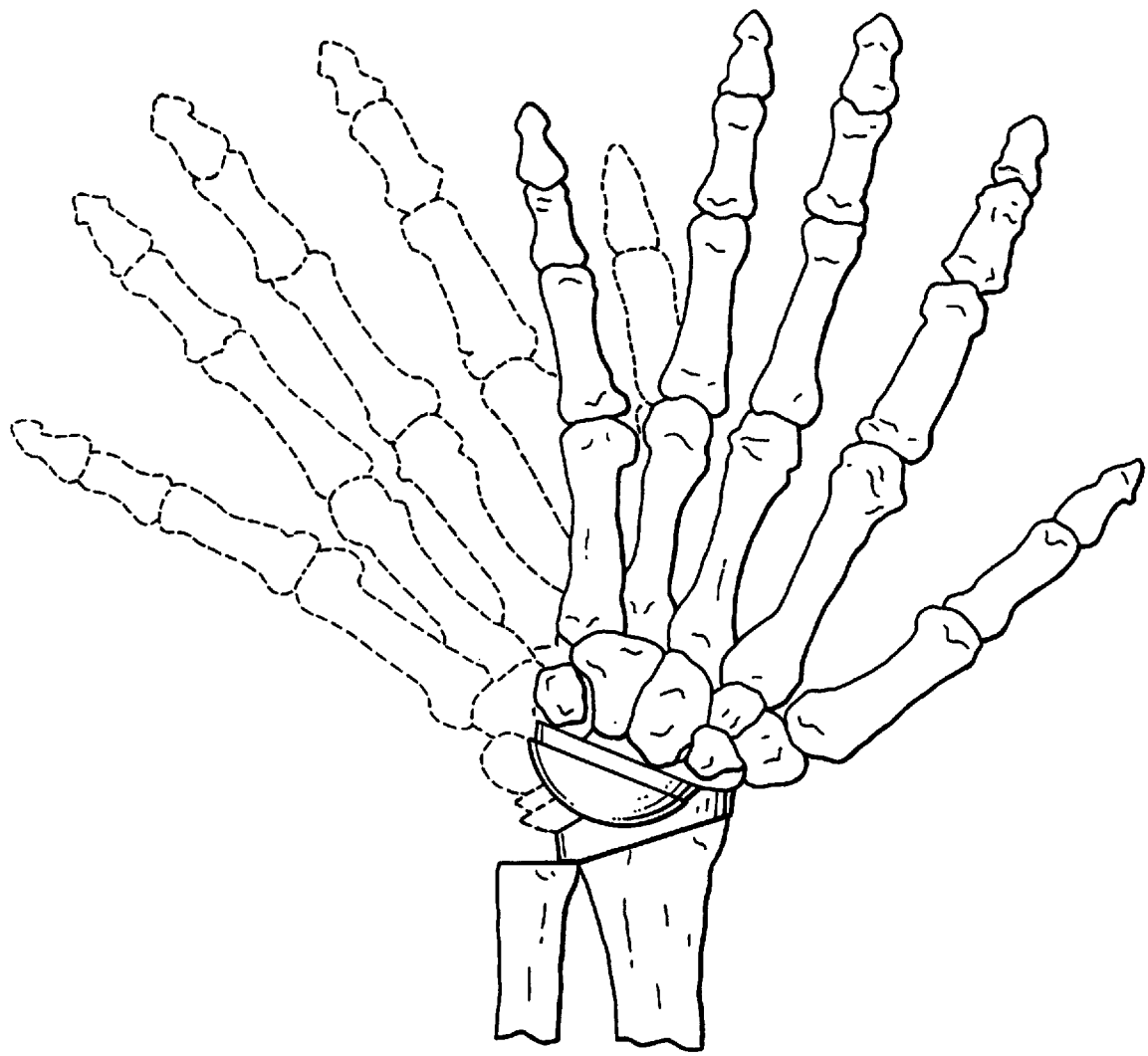
FIG. 19 is a perspective view of the bones of the left hand with a trial wrist implant in place showing the range of motion of the wrists.

A trial reduction is then performed. The stem of a trial carpal component 50 is introduced into the opening in the capitate bone. A drill hole is made through the radial opening in the carpal plate capturing the scaphoid and the trapezoid bones using a 2.5 millimeter drill bit. A 20 millimeter long and 4.5 millimeter or diameter self-taping screw is then inserted to obtain the temporary fixation. A trial radial component is then inserted into the medullary canal of the radius. Trial plastic carpal bearing 124 is slid over the carpal plate and the joint is reduced as shown in FIG. 19. If the joint is too tight, additional bone is removed from the radial until good dorsiflexion, palmarflexion, radial and ulnar deviation is achieved. The wrist should easily stay in neutral position or in the balance state.

When performing a trial reduction, an alternative to the procedure described immediately above is to use a trial set comprising a trial carpal implant component, a trial radial implant component, and a trial carpal bearing set. Both the trial carpal implant component and the trial radial implant component are identical to the implant components which will be permanently implanted during the implant procedure. However, the trial set has the advantage of sizing nine different trial carpal bearings during the "15" process. After the trial carpal component 50 and the trial radial component have been positioned, a trial plastic carpal bearing is slid over the carpal plate and the joint is reduced as shown in FIG. 19. If the joint is too tight, the first trial carpal bearing is removed and a second trial carpal bearing is inserted, the second bearing of either an increased dimension or a decreased dimension depending upon the results of the trial reduction. The trial carpal bearings are made of an acetyl copolymer, a composite material, or any material having similar characteristics. The trial carpal implant component is preferably made of titanium and the radial implant component is preferably made of a cobalt-chrome material. However, the carpal implant component or the radial implant component may be made of any material having similar characteristics, such as a composite material. An advantage to using the trial set during a trial reduction is that the size of the carpal bearing may be precisely selected for the particular implant being performed. This eliminates the necessity of having to remove additional bone from the radial bone in order to achieve a proper fit of the implant. Another advantage of using the trial set during the trial reduction is that the trial set may be reused after proper sterilization has been performed. Sterilization may include autoclaving or any sterilization method which would not dimensionally or physically affect the trial set.

Figure 20:
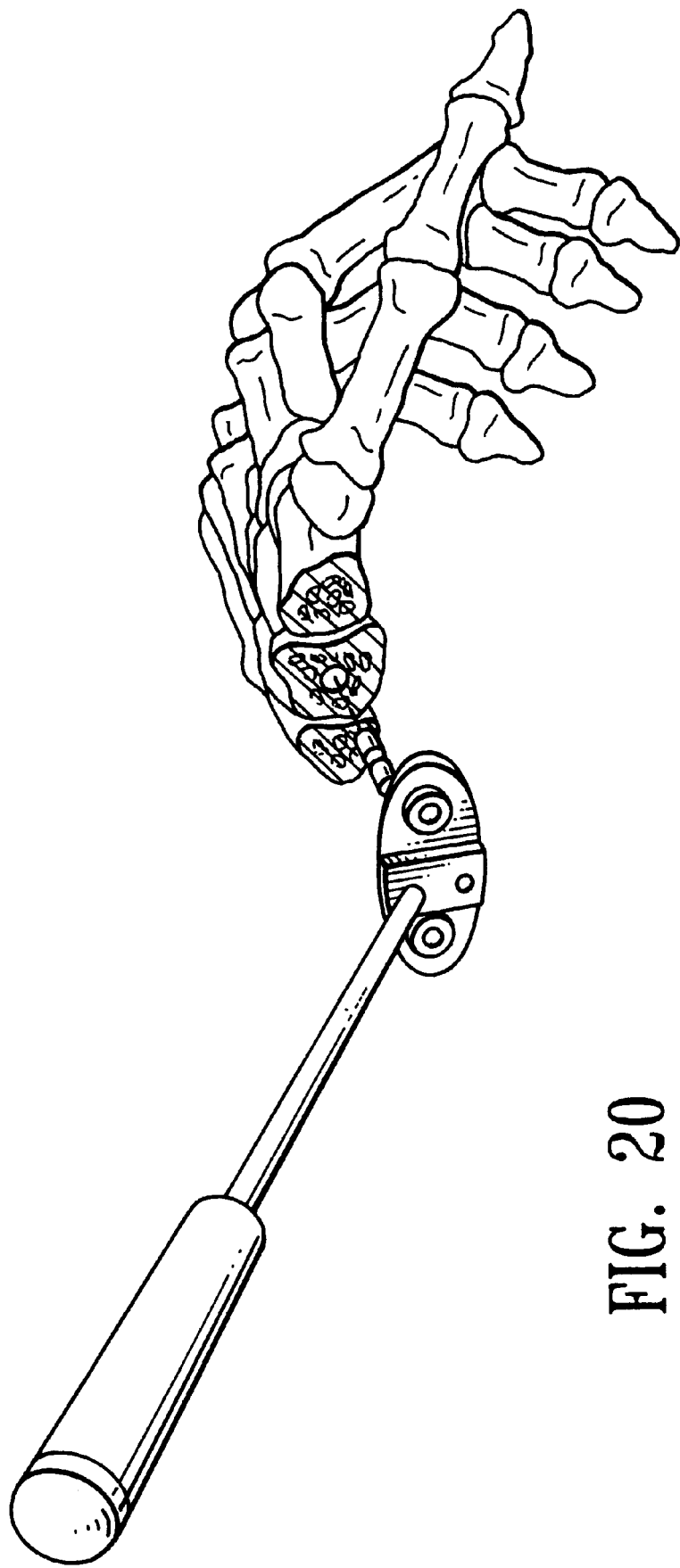
FIG. 20 is a perspective view of the bones of the left hand illustrating the fixation of the carpal component of the prosthetic wrist implant of the present invention.

Next the carpal component fixation is performed. First the wound is irrigated with pulsed lavage. Bone cement is introduced into the central peg hole in the capitate metacarpal complex. For example, in accordance with one embodiment of the present invention, this bone cement comprises methylemethacrylate. The stem of the carpal implant 50 is introduced into this hole and tapped all of the way in as shown in FIG. 20 utilizing the trial bearing 124 and the radial pusher handle 126. It is important to keep the implant flush with the bone margins. Care must be taken to remove excess cement, especially from the intracarpal region. The ulnar side of the plate is then drilled with a 2.5 millimeter bit. Two 4.5 millimeter screws are then inserted through the peripheral holes in the carpal plate 48. The radial screw is longer and could cross the carpal space mediocarpal joint. Since the carpal mediocarpal joint of the fourth and fifth metacarpals are mobile, care should be taken to avoid crossing these joints. (Unless it is necessary for better purchase.) The screws help hold the fragment of the triquetrun and the scaphoid in place and add strength to the carpal fixation. The bone screws 132, 134 shown in FIG. 23 secure the hamate 22 and trapezoid 26, 28 bones respectively. These bones screws may comprise, for example, conventional 4.5 millimeter diameter bone screws which are between 20 and 40 millimeters in length depending on the size of the implant and patient. Cancellous bone graphs obtained from the radius and resected carpal bones are packed into the defects between the carpal bones to obtain a uniform bony fusion.

Figure 21B:
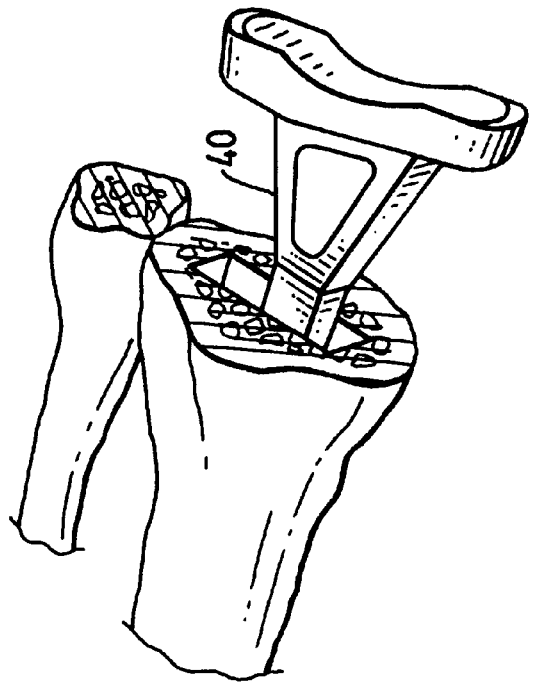
FIGS. 21A–21B are perspective views of the radius and ulnar bones illustrating the technique of fixation of the radial component of the prosthetic wrist implant of the present invention.
Figure 21A:
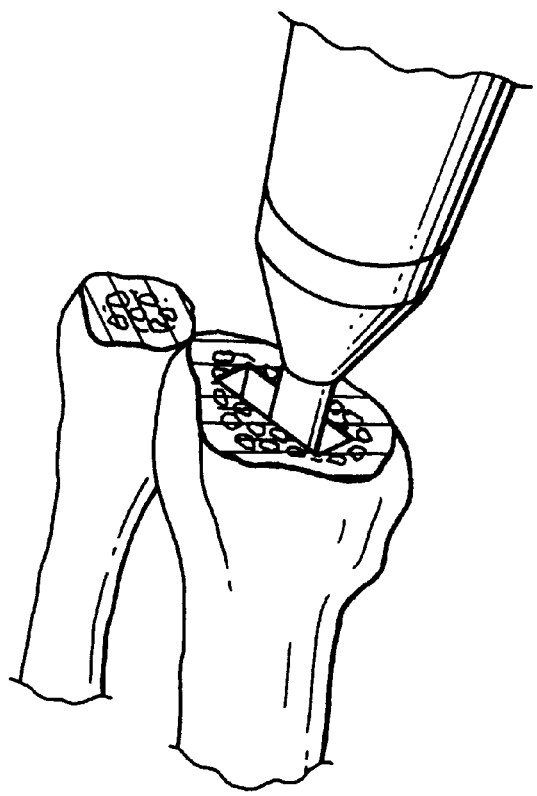

To perform the radial component fixation, a bone plug is inserted into the medullary canal of the radius to act as a cement restricter. The canal is cleaned with pulse lavage and dried. Bone cement is mixed and injected into the canal using a syringe as shown in FIG. 21A. The true radial component 40 is then introduced into the medullary canal as shown in FIG. 21B. It is important to remove all excess cement from the immediate area. Care is taken to place the prosthesis in a valgus position. A varus angle of the component will result in a post-operative ulnar deviation deformity of the hand.

The carpal bearing 42 is then slid over the carpal plate and locked into place using finger pressure or gently taps with an impactor over the carpal implant plate 48. The components are then reduced and the joint is tested for range of motion and stability.

Wound closure is accomplished by first closing the ulnar joint capsule tightly, thereby stabilizing the distal ulnar. The ECU tendon is brought dorsally to obtain additional stability. The capsule of the radial carpal joint is reattached to the distal end of the radius. If the capsule is deficient, one-half of the extensor retinaculum is used to cover the defects. Meticulous closure of the capsule is mandatory to ensure stability in the post operative. The hand is then immobilized in bulky dressing with the wrist in a neutral position for about two to three days. Post operative management will involve removing the sutures after ten days. The wrists should be kept immobilized in a short arm cast for four weeks. After four weeks the cast is removed and the range of motion exercises begun.

Figure 23:
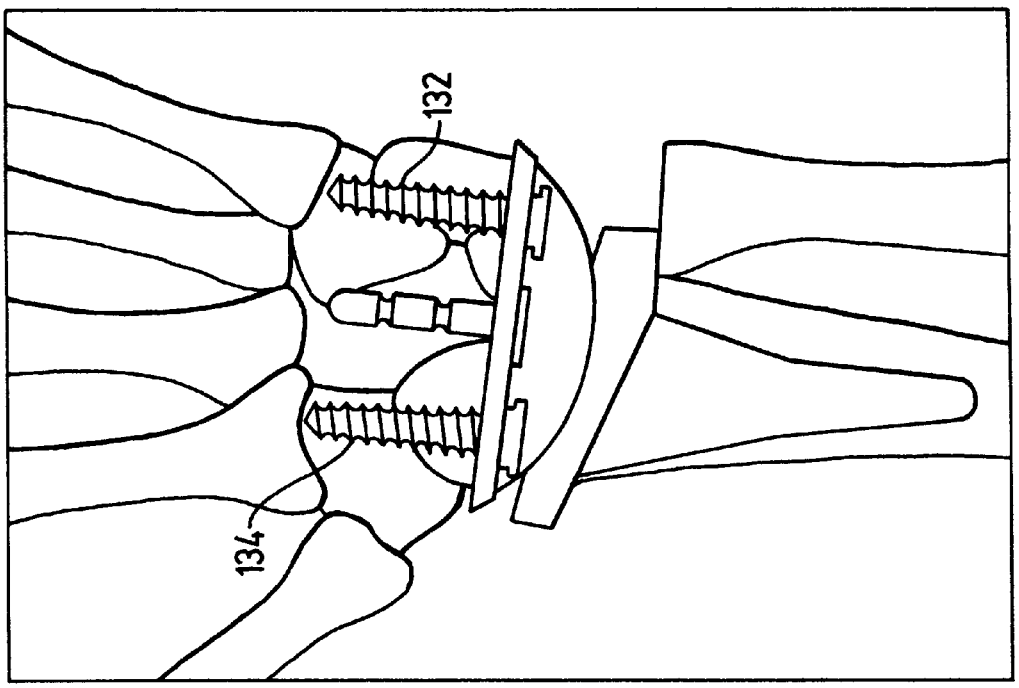
FIG. 23 is a x-ray of the patient's wrist shown in FIG. 22 at 32 months post-operative.
Figure 22:
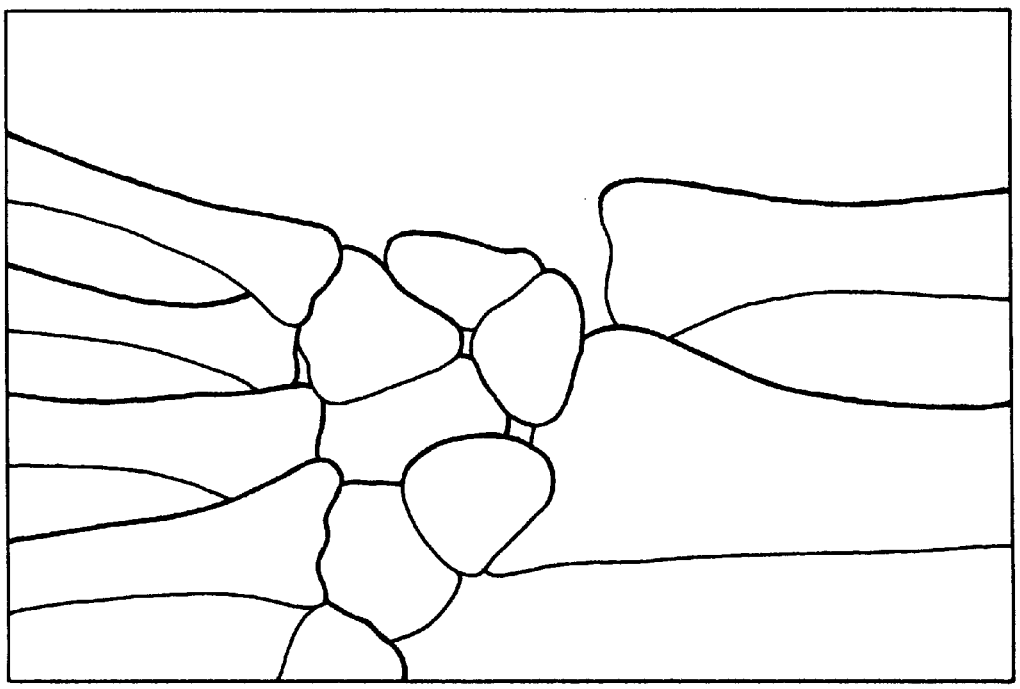
FIG. 22 is a pre-operative x-ray of a patient suffering from radio-carpal arthritis.
Figure 24:
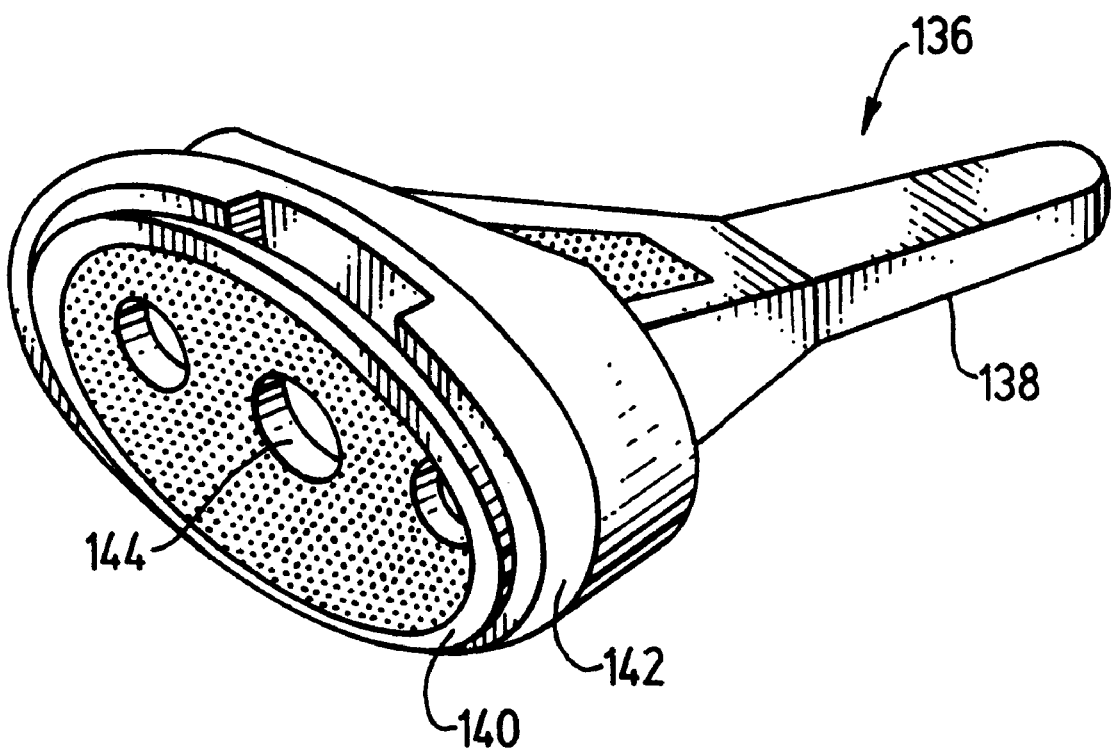
FIG. 24 is a perspective view of a prosthetic wrist implant in accordance with an alternative embodiment of the present invention.
Figure 31C:
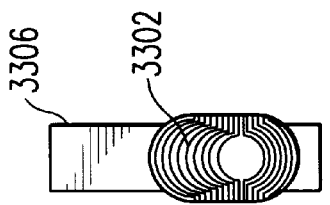
FIGS. 31A–31E are side and end views of a rasp in accordance with one embodiment of the present invention.
Figure 31B:
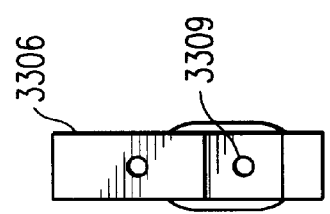
Figure 31A:
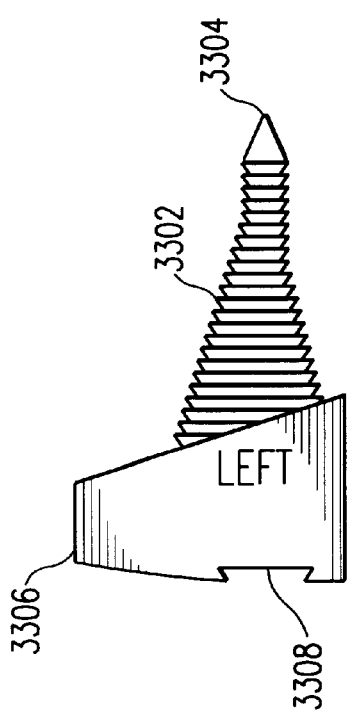
Figure 31E:
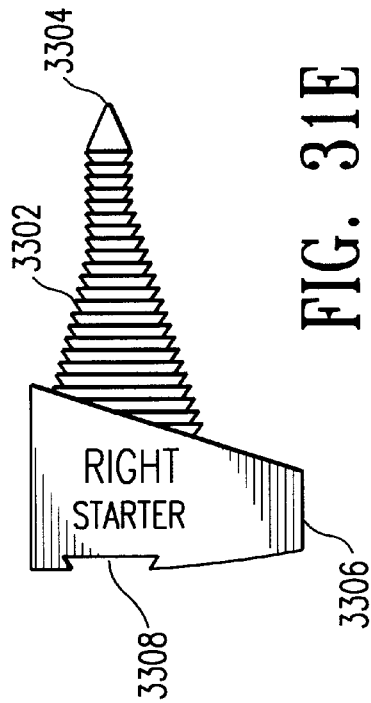
Figure 31D:
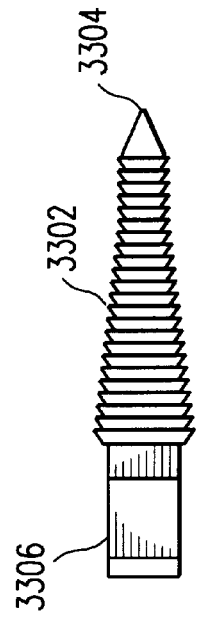

Referring now to FIG. 22, a pre-operative x-ray of a patient suffering from radio-carpal arthritis is shown. FIG. 23 shows the same patient 32 months post-operatively now asymptomatic and with good functional range of motion.

Referring now to FIGS. 24–30, there are shown various views of an alternative embodiment of the prosthetic wrist implant of the present invention. In particular, the implant includes a radial implant component 138, a carpal component 140 and a bearing component 142. As can be seen in FIGS. 24–30, the radial component 138 and bearing component 142 are similar to radial component 40 and 42 respectively shown in FIGS. 2A and 2B. However, in this embodiment the carpal component 140 does not have a carpal post 50. Instead, an opening 144 is used to accept a screw which is inserted into the capitate bone 24 in place of the carpal post 50. Similarly, in accordance with another alternative embodiment (not shown), the radial implant 136 may be secured using at least one screw which is inserted through the radial component into the radial bone 12.

A number of embodiments of the present invention have been described. Nevertheless, it will be understood that various modifications may be made without departing from the spirit and scope of the invention. For example, various materials and alterations in the geometry of the components of the present invention may be utilized from those disclosed without departing from the scope of the present invention as will be clear to one of ordinary skill. Accordingly, it is understood that the invention is not to be limited by the specific illustrated embodiment, but only by the scope of the appended claims.

What is claimed is:

1. A prosthetic wrist implant disposed between a patient's radius and carpal bone complex comprising:
   a radial implant having an elongated concave articular front surface and a back surface;
   a carpal bone implant including a planar base member having a front surface and a generally flat back surface, and a carpal post member projecting from the rear surface into a cavity of the carpal bone complex; and
   an articulating member having a flat bottom surface fastened to the front surface of the base member and an elongated convex articular surface slidably engaging the concave articular surface of the radial implant to permit articulation between the radius and carpal bone complex by the concave and convex articular surfaces, wherein the carpal bone implant planar member has two openings therein, and further comprising a pair of screws inserted through the two openings and into the carpal bone complex.

2. The prosthetic wrist implant of claim 1, wherein the radial implant back surface his a first flat portion and a second flat portion tilted at an angle with respect to the first flat portion.

3. The prosthetic wrist implant of claim 2, wherein the articular front surface of the radial implant and the second flat portion of the radial implant are tilted with respect to the longitudinal axis of the post, whereby the articular surface of the radius is mimicked.

4. A prosthetic wrist implant disposed between a patient's radius and carpal bone complex comprising:
   a radial implant having an elongated concave articular front surface and a back surface;
   a carpal bone implant including a planar base member having a front surface and a generally flat bark surface, and a carpal post member projecting from the rear surface into a cavity of the carpal bone complex; and
   an articulating member having a flat bottom surface fastened to the front surface of the base member and an elongated convex articular surface slidably engaging the concave articular surface of the radial implant to permit articulation between the radius and carpal bone complex by the concave and convex articular surfaces, wherein the articulating member has slotted recesses, and wherein the articulating member engages raised slotted tabs of the carpal implant front surface to securely fasten the articulating member to the carpal implant.

5. The prosthetic wrist implant of claim 1, wherein the carpal post member is inserted into the capitate bone of the carpal bone complex, and wherein a screw is inserted into the trapezoid bone and another screw is inserted into the hamate bone of the carpal bone complex.

6. The prosthetic wrist implant of claim 1, wherein the articulating member is constructed of a plastic material.

7. The prosthetic wrist implant of claim 1, wherein the rear surface of the carpal bone implant abuts a resected surface of the carpal bone complex and the rear surface of the radial implant abuts a resected surface of the radius.

8. A prosthetic wrist implant disposed between a patient's radius and carpal bone complex comprising:
   a radial implant having an elongated concave articular font surface and a back surface, the radial implant also having a radial post member projecting from the back surface into a cavity in the radius;
   a carpal bone implant including a base member having a front surface and a rear surface, the base member having three openings;
   a plurality of screws inserted through the openings for securing the carpal bone implant to the carpal bone complex; and
   an articulating member having a flat bottom surface fastened to the front surface of the base member and an elongated convex articular surface slidably engaging the concave articular surface of the radial implant to permit articulation between the radius and carpal bone complex by the concave articular surface and convex articular surface.

9. The prosthetic wrist implant of claim 8, wherein the radial implant back surface has a first flat portion and a second flat portion tilted at an angle with respect to the first flat portion.

10. The prosthetic wrist implant of claim 9, wherein the articular front surface of the radial implant and the second flat portion of the radial implant are tilted with respect to the longitudinal axis of the post, whereby the articular surface of the radius is mimicked.

11. The prosthetic wrist implant of claim 8, wherein the carpal bone implant front surface has raised slot tabs, the articulating member has slotted recesses, and wherein the slotted recesses of the articulating member engages with the raised slotted tabs of the carpal bone implant front surface to securely fasten the articulating member to the carpal bone implant.

12. The prosthetic wrist implant of claim 8, wherein the radial post member has a generally rectangular cress section.

13. The prosthetic wrist implant of claim 8, wherein at least one screw is inserted through the carpal bone implant base member into the trapezoid bone of the carpal bone complex and at least one screw is inserted through the carpal bone implant base member into the hamate bone of the carpal bone complex.

14. The prosthetic wrist implant of claim 8, wherein the articulating member is constructed of a plastic material.

15. The prosthetic wrist implant of claim 8, wherein the rear surface of the carpal bone implant abuts a resected surface of the carpal bone complex and the rear surface of the radial implant abuts a resected surface of the radius.

16. A method for implanting a prosthetic wrist implant between a patient's radius and carpal bone complex, the method comprising the steps of:

provoiding a radial implant having an elongated, concave, articular front surface and a rear surface;

providing a carpal bone implant having a base member including a front and a rear surface;

resectioning the carpal bone complex along a plane that is perpendicular to the longitudinal axis of the capitate metacarpal bone;

resectioning the radius along a plane which is at an angle with a normal plane that is perpendicular to the longitudinal axis of the radius;

positioning the radial implant adjacent to the radius so that the rear surface of the radial implant abuts the resected radius;

positioning the carpal bone implant adjacent to the carpal bone complex so that the rear surface of the carpal bone implant abuts the resected carpal bone complex; and securing the radial and carpal bone implants to the radius and carpal bone complex respectively, using a fastening device.

17. The method recited in claim 16, wherein the radial implant includes a radial post member projecting from the rear surface of the radial implant, and wherein the method includes the steps of:

reaming an opening in the resected radius which substantially matches the size and shape of the radial post member; and implanting the radial post member into the opening in the resected radius.

18. The method recited in claim 16, wherein the carpal bone implant includes a carpal post member projecting from the rear surface of the base member, and wherein the method includes the steps of:

making an opening in the resected carpal bone complex, wherein the opening is sized to snugly receive the carpal post member; and implanting the carpal post member into the carpal bone complex.

19. A method for implanting a prosthetic wrist implant between a patient's radius and carpal bone complex, the method comprising the steps of:

providing a radial implant having an elongated, concave, articular front surface and a rear surface;

providing a carpal bone implant having a base member including a font and a rear surface;

resecting the carpal bone complex along a plane that is perpendicular to the longitudinal axis of the capitate of the carpal bone complex;

resecting the radius along a plane which is at an angle with a normal plane that is perpendicular to the longitudinal axis of the radius;

positioning a trial prosthetic wrist implant set, comprising the steps of:

positioning a trial radial implant adjacent to the radius so that the rear surface of the radial implant abuts the resected radius;

positioning a carpal bone implant adjacent to the carpal bone complex so that the rear surface of the carpal bone implant abuts the resected carpal bone complex; and securing the radial and carpal bone implants to the radius and carpal bone complex respectively, using a fastening device;

inserting a first carpal bearing between the trial radial and trial carpal bone implants;

checking the fit and articulation of the prosthetic wrist implant, and if the fit and articulation are satisfactory:

a) removing the first trial carpal bearing from between the trial radial and trial carpal bone implants;

b) removing the trial radial implant from the radius; and c) removing the trial carpal bone implant from the caw bone comple; and if the fit and articulation are unsatisfactory;

d) removing the first trial carpal bearing from between the trial radial and trial carpal bone implants;

e) inserting a second trial carpal bearing between the trial radial and trial carpal bone implants;

f) checking the fit and articulation of the prosthetic wrist implant, and if it is unsatisfactory, repeating steps d) through f), and if it is satisfactory;

positioning a radial implant adjacent to the radius so that the rear surface of the radial implant abuts the resected radius;

positioning a carpal bone implant adjacent to the carpal bone complex so that the rear surface of the carpal bone implant abuts the resected carpal bone complex;

inserting a carpal bearing corresponding to the trial carpal bearing used to satisfactorily fit and articulate the trial prosthetic wrist implant; and securing the radial and carpal bone implants to the radius and carpal bone complex, respectively, using a fastening device.

20. The method recited in claim 19, wherein the carpal bone implant includes a carpal post member projecting from the rear surface of the base member, and wherein the method includes the steps of:

making an opening in the resected carpal bone complex, wherein the opening is sized to snugly receive the carpal post member; and implanting the carpal post member into the carpal bone complex.

21. The method recited in claim 19, wherein the radial bone implant includes a radial post member projecting from the rear surface of the radial implant, and wherein the method includes the steps of:

making an opening in the resected radius, wherein the opening is sized to snugly receive the radial post member; and implanting the radial post member into the radius.

22. The method recited in claim 19, wherein the carpal bone implant includes a carpal post member projecting from the rear surface of the base member, and the radial bone implant includes a radial post member, wherein the method includes the steps of:

making an opening in the resected carpal bone complex, wherein the opening is sized to snugly receive the carpal post member;

making an opening in the resected radius, wherein the opening is sized to snugly receive the radial post member;

implanting the carpal post member into the carpal bone complex; and implanting the radial post member into the radius.

* * * * *